(12) United States Patent
Edagwa et al.

(10) Patent No.: US 11,117,904 B2
(45) Date of Patent: Sep. 14, 2021

(54) COMPOSITIONS AND METHODS FOR THE DELIVERY OF THERAPEUTICS

(71) Applicants: ViiV Healthcare Company, Wilmington, DE (US); Board of Regents of University of Nebraska, Lincoln, NE (US)

(72) Inventors: Benson J. Edagwa, Lincoln, NE (US); Howard E. Gendelman, Lincoln, NE (US); Brian Alvin Johns, Research Triangle Park, NC (US)

(73) Assignees: ViiV Healthcare Company, Wilmington, DE (US); Board of Regents of University of Nebraska, Lincoln, NE (US)

( * ) Notice: Subject to any disclaimer, the term of this patent is extended or adjusted under 35 U.S.C. 154(b) by 421 days.

(21) Appl. No.: 16/304,759

(22) PCT Filed: Jun. 22, 2017

(86) PCT No.: PCT/US2017/038693
§ 371 (c)(1),
(2) Date: Nov. 27, 2018

(87) PCT Pub. No.: WO2017/223280
PCT Pub. Date: Dec. 28, 2017

(65) Prior Publication Data
US 2021/0230186 A1    Jul. 29, 2021

Related U.S. Application Data

(60) Provisional application No. 62/353,736, filed on Jun. 23, 2016.

(51) Int. Cl.
*C07D 498/14* (2006.01)
*A61K 47/10* (2017.01)
*A61P 31/18* (2006.01)
*A61K 47/69* (2017.01)
*B82Y 5/00* (2011.01)

(52) U.S. Cl.
CPC .......... *C07D 498/14* (2013.01); *A61K 47/10* (2013.01); *A61K 47/6929* (2017.08); *A61P 31/18* (2018.01); *B82Y 5/00* (2013.01)

(58) Field of Classification Search
CPC .. C07D 498/14; A61K 47/6929; A61K 47/10; A61P 31/18; B82Y 5/00
USPC .................................................... 514/230.2
See application file for complete search history.

(56) References Cited

U.S. PATENT DOCUMENTS

| | | |
|---|---|---|
| 2013/0171214 A1 | 7/2013 | Mundhra et al. |
| 2014/0011995 A1 | 1/2014 | Sumino et al. |
| 2014/0221378 A1 | 8/2014 | Miyazaki et al. |
| 2015/0232479 A1 | 8/2015 | Johns et al. |

*Primary Examiner* — Kristin A Vajda
(74) *Attorney, Agent, or Firm* — J. Scott Young

(57) ABSTRACT

The present invention provides compositions and methods for the delivery of antivirals to a cell or subject.

28 Claims, 7 Drawing Sheets

COMPOSITIONS AND METHODS FOR THE DELIVERY OF THERAPEUTICS

FIELD OF THE INVENTION

Figure 1:
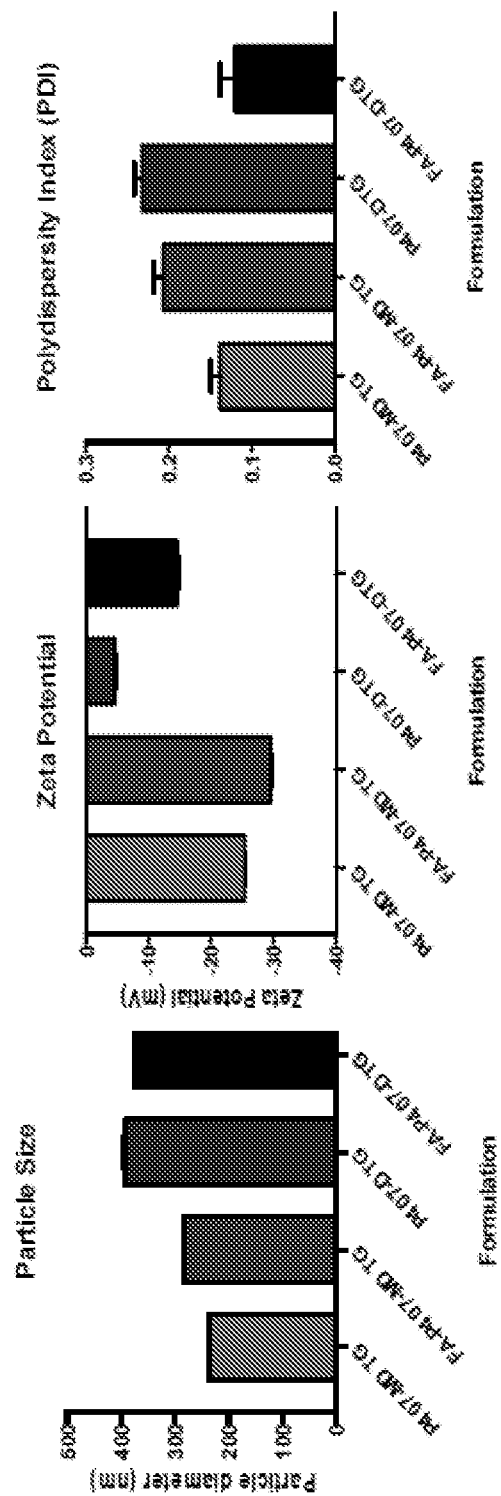

The present invention relates generally to the delivery, cell entry and retention of therapeutics. More specifically, the present invention relates to compositions and methods for the delivery and cell-based retention of therapeutic agents to a patient for the treatment and prevention of a viral infection.

BACKGROUND OF THE INVENTION

The need to improve the bioavailability, pharmacokinetics, pharmacodynamics, tissue distribution, cytotoxicities, and interval dosing of antiretroviral therapy (ART) in the treatment of human immunodeficiency virus (HIV) infection is notable (Broder, S. (2010) Antivir. Res., 85:1-18; Este et al. (2010) Antivir. Res., 85:25-33; Moreno et al. (2010) J. Antimicrob. Chemother., 65:827-835). Since the introduction of ART, incidences of both mortality and co-morbidities associated with HIV-1 infection have decreased dramatically. However, ART limitations abound which prevent full suppression of viral replication, reductions in drug-resistance patterns, biodistribution, pharmacokinetics (PK) and associated morbidities in HIV-infected individuals. These limitations also include drug PK and biodistribution, (Garvie et al. (2009) J. Adolesc. Health 44:124-132; Hawkins, T. (2006) AIDS Patient Care STDs 20:6-18; Royal et al. (2009) AIDS Care 21:448-455). Moreover, despite effective drug combinations, HIV continues to replicate at low levels in reservoir sites that include, but are not limited to, the lymph nodes, bone marrow, gut-associated lymphoid tissues, spleen and central nervous system (Pomerantz, R. J., (2002) Clin. Infect. Dis., 34(1):91-97; Blankson et al. (2002) Annu. Rev. Med., 53:557-593). Such limitations affect pathways towards sterilization/eradication of HIV-1 infection from an infected human host.

Since antiretroviral drugs (ARVs) are quickly eliminated from the body and do not thoroughly penetrate all organs, dosing schedules tend to be complex and involve the continuous administration of large amounts of drug. Patients have difficulty properly following therapy guidelines leading to suboptimal adherence and increased risk of developing viral resistance, which can result in treatment failure and accelerated progression of disease (Danel et al. (2009) J. Infect. Dis. 199:66-76). For HIV-infected patients who also experience psychiatric and mental disorders and/or drug abuse, proper adherence to therapy is even more difficult (Meade et al. (2009) AIDS Patient Care STDs 23:259-266; Baum et al. (2009) J. Acquir. Immune Defic. Syndr., 50:93-99). While long-acting injectable formulations of rilpivirine and cabotegravir (CAB-LAP) have allowed for once-monthly injection for HIV suppression and prevention (Andrews et al. (2014) Science 343:1151-1154; Cohen, J. (2014) Science 343:1067; Spreen et al. (2013) Curr. Opin. HIV AIDS 8:565-571), these therapies still require high doses and high injection volumes.

Accordingly, there is a need for drug delivery systems that optimize cell uptake and retention, improve intracellular stability, reduce injection volumes, extend drug release, extend plasma half-life, maintain antiretroviral efficacy, and limit cytotoxicity.

SUMMARY OF THE INVENTION

In accordance with the instant invention, integrase inhibitor prodrugs are provided. In a particular embodiment, nanoparticles comprising at least one integrase inhibitor prodrug and at least one surfactant are provided.

In a particular embodiment, the integrase inhibitor prodrug has been modified to be more hydrophobic. In a particular embodiment, the integrase inhibitor is conjugated (e.g., at the hydroxyl (—OH) group, optionally via a linker (e.g., a carbonyl (e.g., after an acylation reaction))) with a hydrophobic aliphatic or alkyl as represented by the formula (I-A):

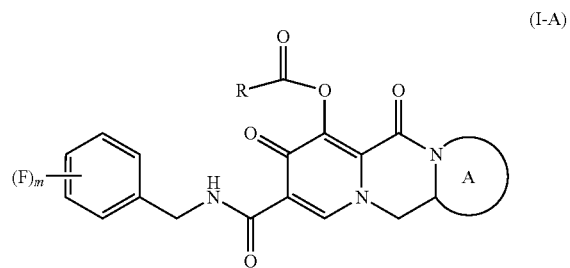

and pharmaceutically acceptable salts thereof, wherein m is 0-3 and R is the aliphatic group. In a particular embodiment, R is R is (L)n-R', L is selected from $C_3$-$C_{30}$ alkyl optionally substituted by 1-5 heteroatoms selected from N, S, and O, and $C_3$-$C_{30}$ alkyenyl optionally substituted by 1-5 heteroatoms selected from N, S, and O, n is 0 or 1, and $R^1$ is selected from H, aryl, cycloalkyl, and cycloalkenyl.

In a particular embodiment, the integrase inhibitor prodrug is a dolutegravir (S/GSK1349572, Tivicay®) prodrug. In a particular embodiment, the integrase inhibitor prodrug is a cabotegravir (S/GSK1265744) prodrug. In a particular embodiment, the integrase inhibitor is a bictegravir prodrug. In a particular embodiment, the integrase inhibitor prodrug is crystalline or amorphous.

According to another embodiment of the invention, there is provided a nanoparticle comprising at least one integrase inhibitor prodrug and a surfactant. In a particular embodiment, the surfactant is an amphiphilic block copolymer, polysorbate, phospholipid, derivative thereof, or combination thereof. In a particular embodiment, the surfactant is an amphiphilic block copolymer (e.g., poloxamer P407). In a particular embodiment, a surfactant of the nanoparticle/nanoformulation is linked to at least one targeting ligand. Indeed, antibodies and peptides can facilitate reservoir-eliminating interventions based on their specificity and facilitating of targeting reservoir sites for low level infection. One example is folic acid. An individual nanoparticle may comprise targeted and non-targeted surfactants.

Pharmaceutical compositions comprising at least one nanoparticle and/or prodrug of the instant invention and at least one pharmaceutically acceptable carrier are also provided.

According to another aspect of the instant invention, methods and uses for treating a disease or disorder (e.g., a viral, particularly a retroviral (e.g., HIV) infection) in a subject are provided. In a particular embodiment, the method comprises administering to the subject at least one prodrug and/or nanoparticle/nanoformulation of the instant invention. In a particular embodiment, the method further comprises administering at least one further therapeutic agent or therapy for the disease or disorder, e.g., at least one additional anti-HIV compound.

According to another aspect of the instant invention, methods and uses for inhibiting a disease or disorder (e.g., a viral, particularly a retroviral (e.g., HIV) infection) in a subject are provided. In a particular embodiment, the method comprises administering to the subject at least one prodrug and/or nanoparticle/nanoformulation of the instant invention. In a particular embodiment, the method further comprises administering at least one further therapeutic agent or therapy for the disease or disorder, e.g., at least one additional anti-HIV compound.

According to another aspect of the instant invention, methods and uses for preventing a disease or disorder (e.g., a viral, particularly a retroviral (e.g., HIV) infection) in a subject are provided. In a particular embodiment, the method comprises administering to the subject at least one prodrug and/or nanoparticle/nanoformulation of the instant invention. In a particular embodiment, the method further comprises administering at least one further therapeutic agent or therapy for the disease or disorder, e.g., at least one additional anti-HIV compound.

According to another aspect of the instant invention, there is provided the use of the prodrugs and/or nanoparticles of the invention in the preparation of medicaments for use in the treatment of a disease or disorder (e.g., a viral, particularly a retroviral (e.g., HIV) infection) in a subject are provided. In a particular embodiment, the method comprises administering to the subject at least one prodrug and/or nanoparticle/nanoformulation of the instant invention. In a particular embodiment, the method further comprises administering at least one further therapeutic agent or therapy for the disease or disorder, e.g., at least one additional anti-HIV compound.

BRIEF DESCRIPTIONS OF THE DRAWING

FIG. 1 provides graphs showing the characterization of nanoparticle by dynamic light scattering. Specifically, the particle size, zeta potential, and polydispersity index are shown for the modified dolutegravir (DTG) prodrug (MDTG) formulation (P407-MDTG), the folic acid (FA) labeled MDTG formulation (FA-P407-MDTG), the native drug DTG formulation (P407-DTG), and the native drug formulation labeled with FA (FA-P407-DTG).

Figure 2A:
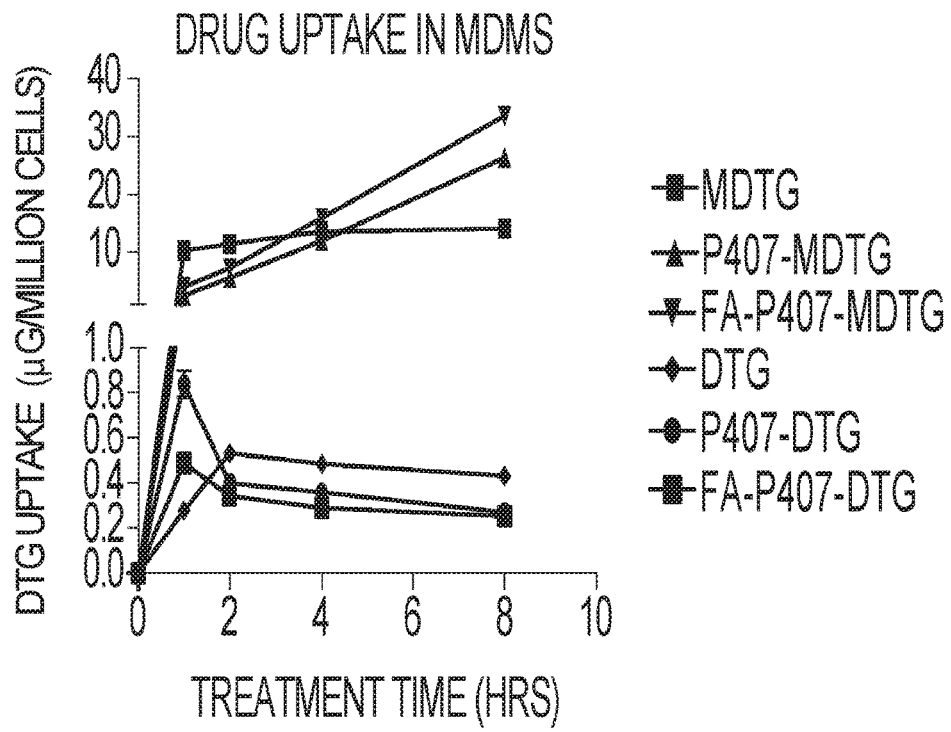
Figure 2B:
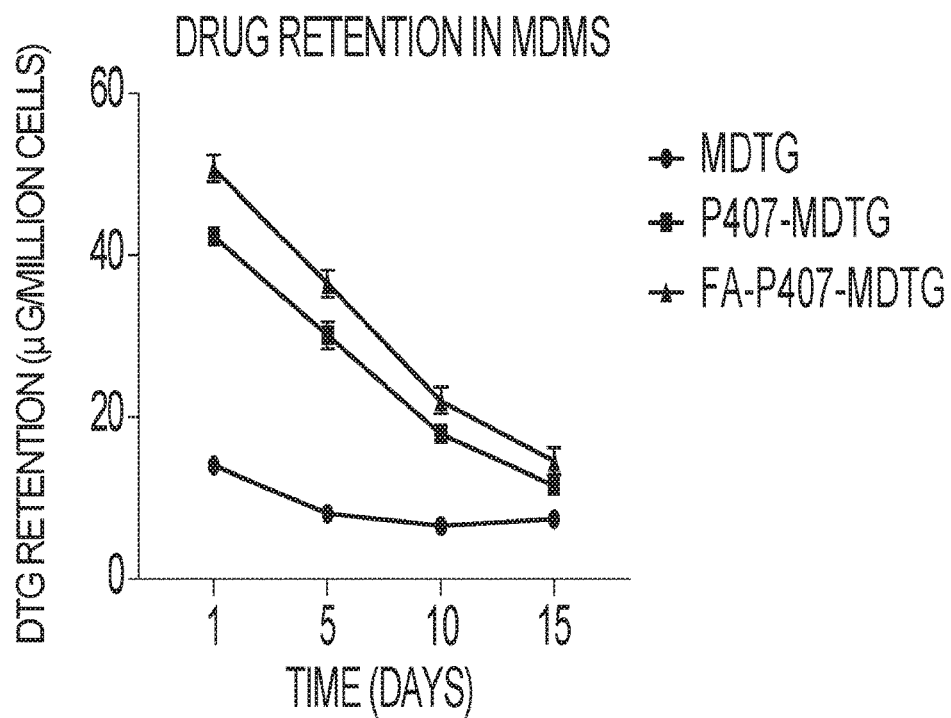
Figure 2C:
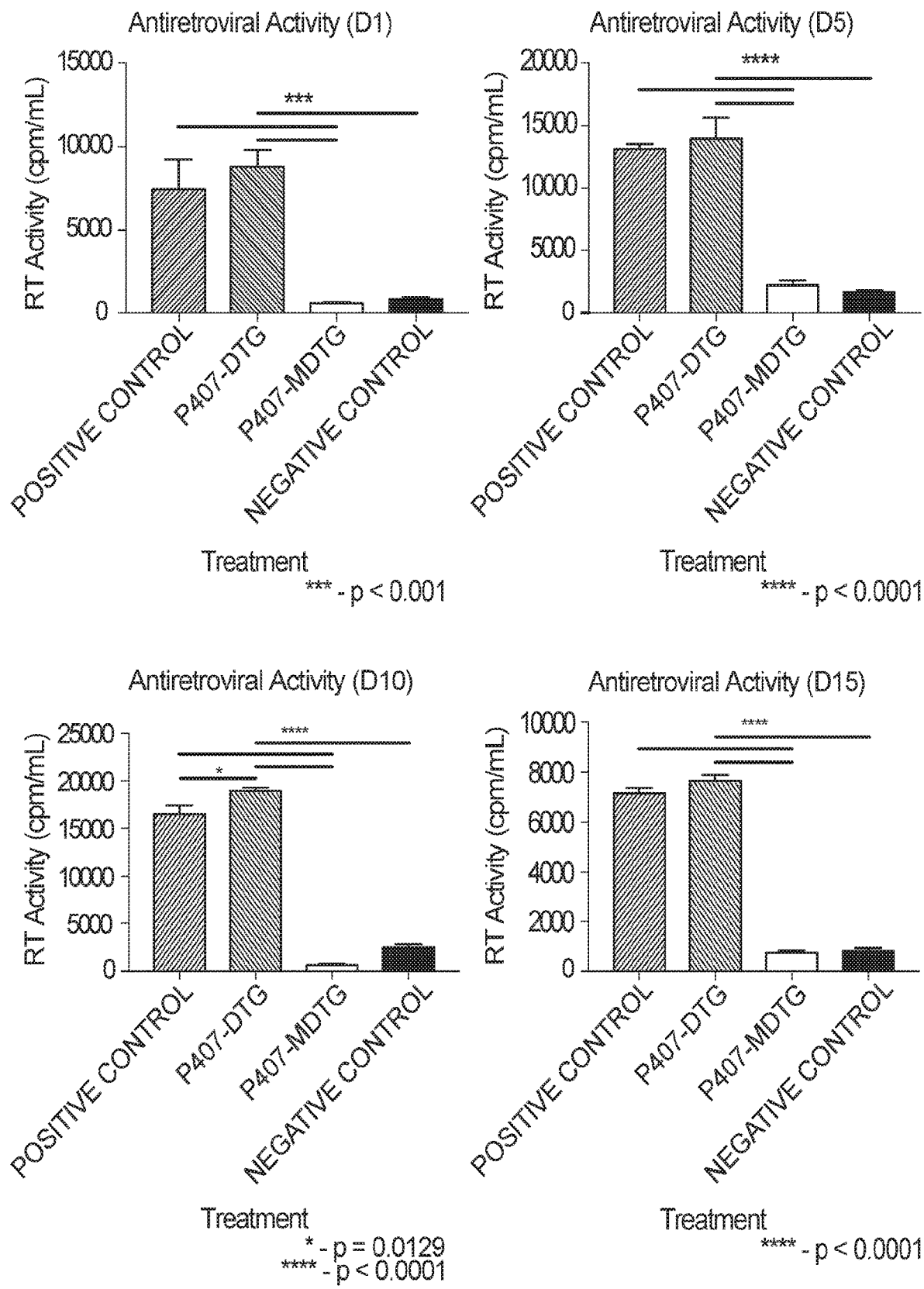
Figure 2D:
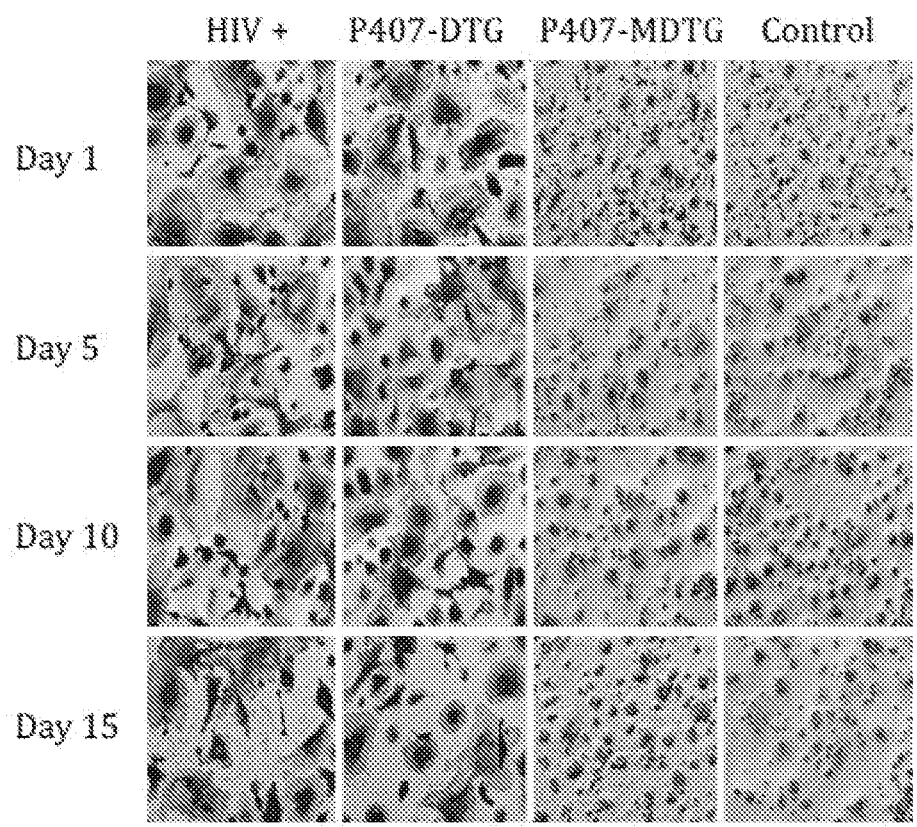

FIG. 2A shows the uptake of DTG by monocytes administered prodrug MDTG, P407-MDTG, FA-P407-MDTG, native drug DTG, P407-DTG, or FA-P407-DTG. FIG. 2B shows the retention of DTG by monocytes treated with MDTG, P407-MDTG, or FA-P407-MDTG. FIG. 2C provides graphs of HIV reverse transcriptase activity (at days 1, 8, 10, and 15) in monocytes infected with HIV (positive control), mock infected (negative control), or infected with HIV and treated with P407-DTG or P407-MDTG. FIG. 2D provides images of p24 staining of monocytes infected with HIV (HIV+), mock infected (control), or infected with HIV and treated with P407-DTG or P407-MDTG.

Figure 3:
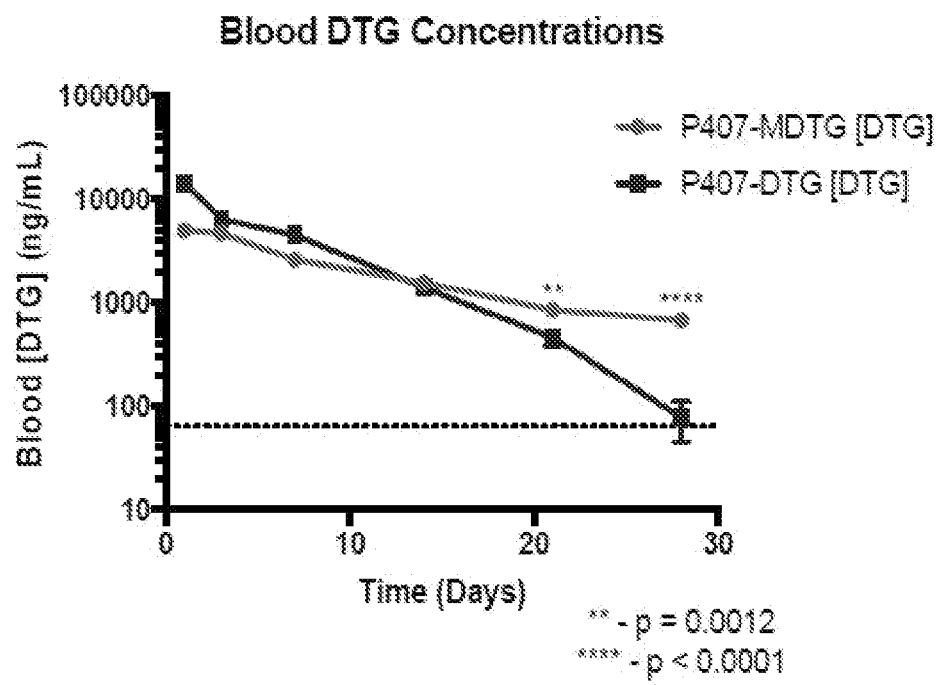

FIG. 3 provides a graph of the blood levels of DTG in mice treated with P407-MDTG or P407-DTG.

Figure 4A:
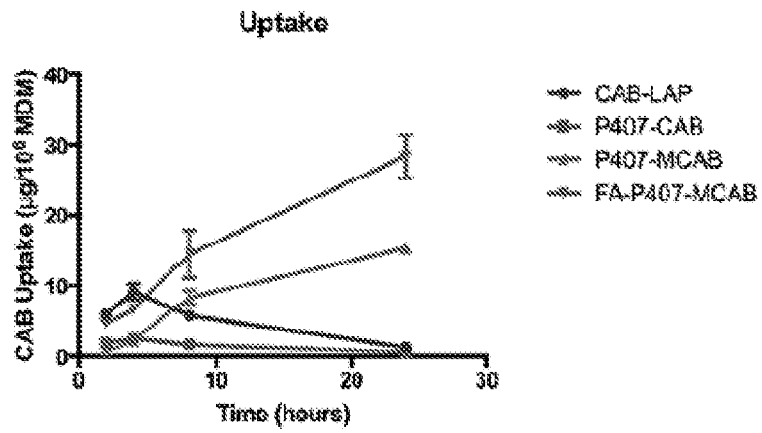
Figure 4B:
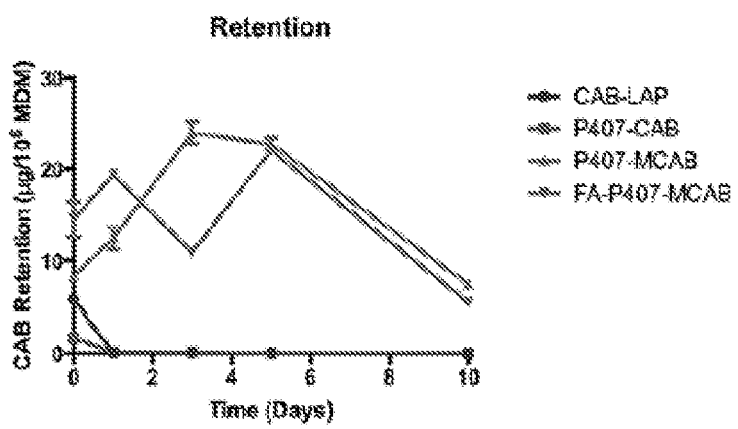
Figure 4C:
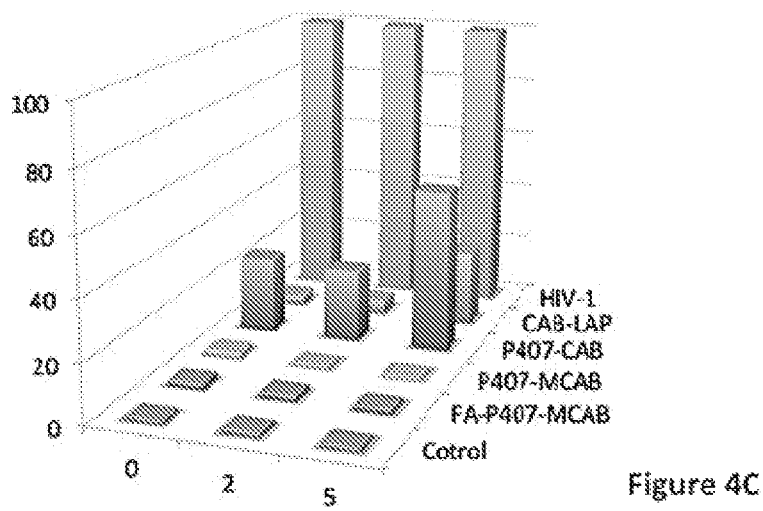
Figure 4D:
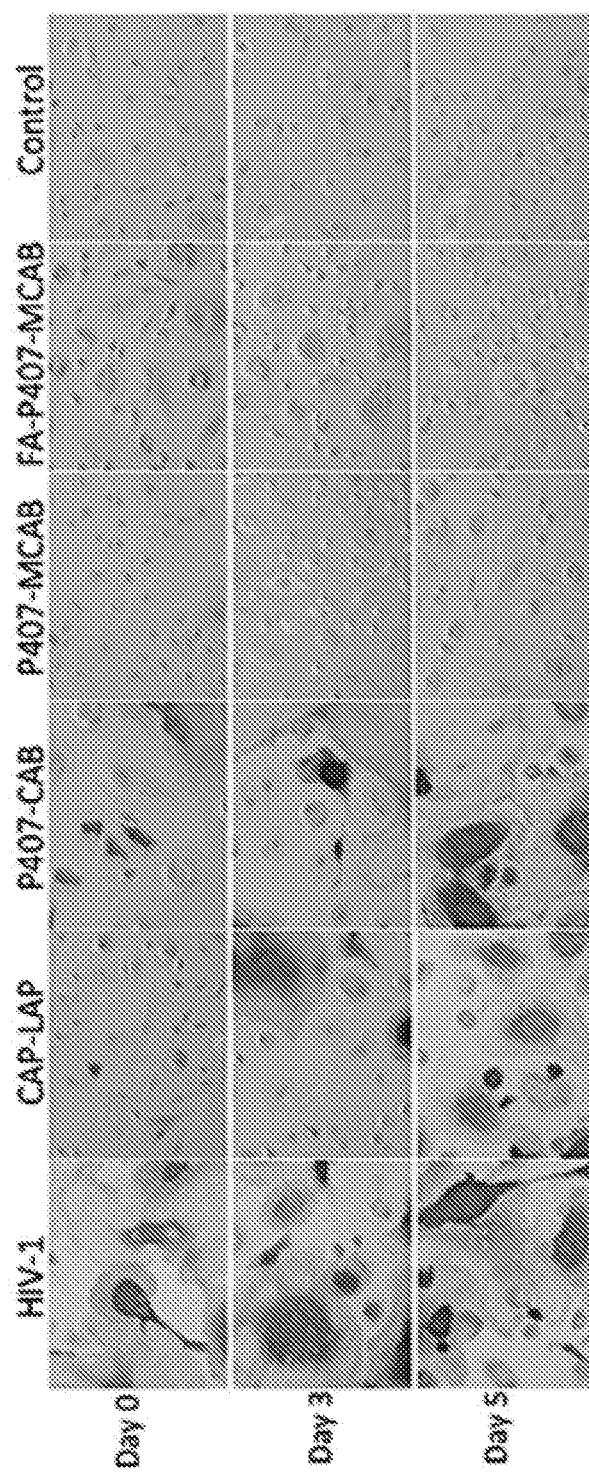

FIG. 4A shows the uptake of cabotegravir (CAB) by monocytes administered long acting parenteral CAB (CAB-LAP), the native drug CAB formulation (P407-CAB), modified CAB prodrug (MCAB) formulation (P407-MCAB), and folic acid (FA) labeled MCAB formulation (FA-P407-MCAB). FIG. 4B shows the retention of CAB by monocytes treated with CAB-LAP, P407-CAB, P407-MCAB, or FA-P407-MCAB. FIG. 4C provides graphs of HIV reverse transcriptase activity (at days 0, 2, and 5) in monocytes infected with HIV (HIV-1), mock infected (control), or infected with HIV and treated with CAB-LAP, P407-CAB, P407-MCAB, or FA-P407-MCAB. FIG. 4D provides images of p24 staining of monocytes infected with HIV (HIV-1), mock infected (control), or infected with HIV and treated with CAB-LAP, P407-CAB, P407-MCAB, or FA-P407-MCAB.

DETAILED DESCRIPTION OF THE INVENTION

Treatments of viral infections, particularly HIV infections, which are currently available, include inhibitors of viral entry, nucleoside reverse transcriptase, nucleotide reverse transcriptase, integrase, and protease. Resistance is linked to a shortened drug half-life, the viral life cycle, and rapid mutations resulting in a high genetic variability. Combination ART which are considered "cocktail" therapy, have gained substantial attention. Benefits include decreased viral resistance, limited toxicities, improved adherence to therapeutic regimens and sustained antiretroviral efficacy. Combination therapies minimize potential drug resistance by suppressing viral (e.g., HIV) replication, thereby reducing spontaneous resistant mutants. Treatment failure is attributed, in part, to the short drug half-life. Furthermore, failure can also be attributed, in part, to limited access to tissue and cellular viral reservoirs, thereby precluding viral eradication efforts. To these ends, the development of cell and tissue targeted nanoformulated prodrug (nanoparticle) platforms are of considerable interest in the management of viral (e.g., HIV) infections. Pre-exposure prophylaxis (PrEP) is another strategy used in the management of viral (e.g., HIV) transmission. For example, TRUVADA® (tenofovir/emtricitabine) has been approved for pre-exposure prophylaxis against HIV infection. Additionally, the combination of lamivudine and zidovudine (COMBIVIR®) has been used as pre-exposure prophylaxis and post-exposure prophylaxis.

Traditional dosage forms of ARVs are characterized by high pill burden that lead to poor adherence. Targeted prodrug nanoparticles will improve drug biodistribution and enhance the therapeutic efficacy and the lower dosage will reduce side effects such as systemic toxicity. Further, single drug treatments may cause high genetic variability of HIV and drug resistance. In contrast, targeted combination therapeutic strategies will decrease viral resistance, improve the quality of life, and increase survival time.

The prodrugs and nanoformulated prodrugs (nanoparticles) provided herein have numerous superior properties including, without limitation, extended drug half-life, increased hydrophobicity, improved protein binding capacity, improved biodistribution, improved plasma half-life, and increased antiviral efficacy. This will benefit people who have to receive daily high doses or even several doses a day, since lower dosage with less dosing frequency would not only decrease the side effects, but also be convenient to the patients. The prodrugs and nanoformulated prodrugs (nanoparticles) provided herein may also be used as a post-exposure treatment and/or pre-exposure prophylaxis (e.g., for people who are at high risk of contracting HIV-1). In other words, the prodrugs and nanoparticles of the instant invention and their combination may be used to prevent a viral infection (e.g., HIV infection) and/or treat or inhibit an acute or long term viral infection (e.g., HIV infection). While the prodrugs and nanoparticles of the instant invention are generally described as ARVs, the prodrugs and nanoformulations of the instant invention are also effective against other microbial or viral infections including, without limitation: retroviruses, lentiviruses, hepatitis viruses (e.g., hepatitis B virus (HBV), hepatitis C virus (HCV) (Tavis et al. (2013) PLoS Pathog., 9(1):e1003125)), herpesviruses (e.g., herpes simplex virus (HSV), HSV-1, HSV-2 (Yan et al.

(2014) 5(4):e01318-14), and Ebola virus. The prodrugs and nanoformulations of the instant invention are also effective against other microbial infections such as *Mycobacterium tuberculosis* or for the treatment of a retrovirus (e.g., HIV) in a subject co-infected with *Mycobacterium tuberculosis*.

In accordance with the instant invention, integrase inhibitor prodrugs are provided, wherein the integrase inhibitor has been modified to be more hydrophobic. The integrase inhibitor prodrugs of the instant invention, particularly the nanoformulations thereof, have improved extended drug half-life, increased hydrophobicity, improved protein binding capacity, increased antiviral efficacy, biodistribution, and plasma half-life compared to native drug. In a particular embodiment, the integrase inhibitor prodrugs comprise the integrase inhibitor conjugated to a hydrophobic moiety through a hydrolyzable bond, particularly as ester bond. In a particular embodiment, the integrase inhibitor is conjugated, optionally via a linker, (e.g., at an —OH group; e.g., via an acylation reaction) with an aliphatic group or an alkyl (e.g., the R group in structures herein). In a particular embodiment, the alkyl or aliphatic group is hydrophobic. In a particular embodiment, the aliphatic group or alkyl comprises about 3 to about 30 carbons, about 4 to about 28 carbons, about 4 to about 24 carbons, about 12 to about 18 carbons, about 12 to about 14 carbons, or about 13 carbons (e.g., in the main chain of the alkyl or aliphatic group). In a particular embodiment, the aliphatic group is a C4-C24 unsaturated or saturated aliphatic carbon chain. The aliphatic chain may be substituted with at least one (e.g., about 1 to about 5 or about 1 to about 3) heteroatoms (e.g., O, N, or S). In a particular embodiment, the aliphatic chain is a fatty acid (saturated or unsaturated) residue. In a particular embodiment, the fatty acid is unsaturated. Examples of fatty acids include, without limitation: caprylic acid, capric acid, lauric acid, myristic acid, palmitic acid, stearic acid, arachidic acid, behenic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, and docosahexaenoic acid. In a particular embodiment, the fatty acid is myristic acid.

According to an alternative embodiment, the prodrugs of the invention are represented as compound of the formula I-A

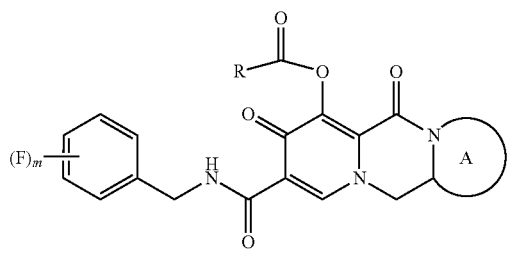

(I-A)

and pharmaceutically acceptable salts thereof wherein ring A is selected from

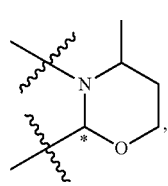

(II-A)

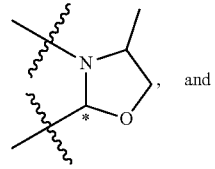

(II-B)

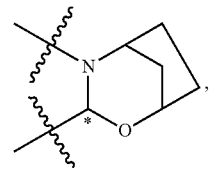

(II-C)

the stereochemistry of an asymmetric carbon represented by * shows R- or S-configuration, or a mixture thereof,
m is 0, 1, 2, or 3,
R is (L)n-R$^1$,
L is selected from C$_3$-C$_{30}$ alkyl optionally substituted by 1-5 heteroatoms selected from N,
S, and O, and C$_3$-C$_{30}$ alkyenyl optionally substituted by 1-5 heteroatoms selected from N,
S, and O,
n is 0 or 1, and
R$^1$ is selected from H, aryl, cycloalkyl, and cycloalkenyl.

In a particular embodiment, the DTG prodrug has the following formula:

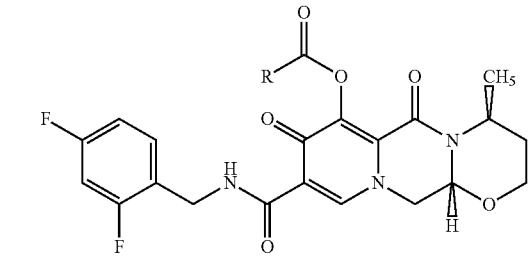

wherein R is an aliphatic group or an alkyl. In a particular embodiment, the alkyl or aliphatic group is hydrophobic. In a particular embodiment, the aliphatic group or alkyl comprises about 3 to about 30 carbons, about 4 to about 28 carbons, about 4 to about 28 carbons, about 12 to about 18 carbons, about 12 to about 14 carbons or about 13 carbons (e.g., in the main chain of the alkyl or aliphatic group). In a particular embodiment, R is a C4-C24 unsaturated or saturated aliphatic chain. The aliphatic may be substituted with at least one (e.g., about 1 to about 5 or about 1 to about 3) heteroatoms (e.g., O, N, or S). In a particular embodiment, R is the residue (that portion of the fatty acid not including the ester end-group) alkyl chain of a fatty acid (saturated or unsaturated). In a particular embodiment, the fatty acid is unsaturated. Examples of fatty acids include, without limitation: caprylic acid, capric acid, lauric acid, myristic acid, palmitic acid, stearic acid, arachidic acid, behenic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, and docosahexaenoic acid. In a particular embodiment, the fatty acid is myristic acid.

In a particular embodiment, the CAB prodrug has the following formula:

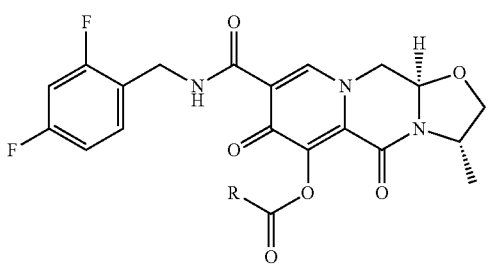

wherein R is an aliphatic group or an alkyl. In a particular embodiment, the alkyl or aliphatic group is hydrophobic. In a particular embodiment, the aliphatic group or alkyl comprises about 3 to about 30 carbons, about 4 to about 28 carbons, about 4 to about 28 carbons, about 12 to about 18 carbons, about 12 to about 14 carbons or about 13 carbons (e.g., in the main chain of the alkyl or aliphatic group). In a particular embodiment, R is a C4-C24 unsaturated or saturated aliphatic chain. The aliphatic may be substituted with at least one (e.g., about 1 to about 5 or about 1 to about 3) heteroatoms (e.g., O, N, or S). In a particular embodiment, R is the residue (that portion of the fatty acid not including the ester end-group) alkyl chain of a fatty acid (saturated or unsaturated). In a particular embodiment, the fatty acid is unsaturated. Examples of fatty acids include, without limitation: caprylic acid, capric acid, lauric acid, myristic acid, palmitic acid, stearic acid, arachidic acid, behenic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, and docosahexaenoic acid. In a particular embodiment, the fatty acid is myristic acid.

In a particular embodiment, the BIC prodrug has the following formula:

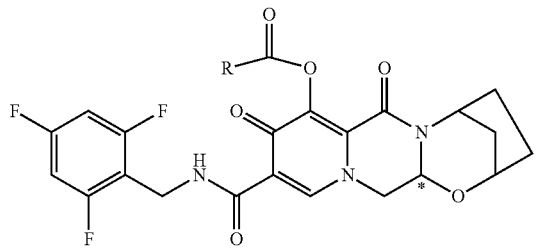

wherein R is an aliphatic group or an alkyl. In a particular embodiment, the alkyl or aliphatic group is hydrophobic. In a particular embodiment, the aliphatic group or alkyl comprises about 3 to about 30 carbons, about 4 to about 28 carbons, about 4 to about 28 carbons, about 12 to about 18 carbons, about 12 to about 14 carbons or about 13 carbons (e.g., in the main chain of the alkyl or aliphatic group). In a particular embodiment, R is a C4-C24 unsaturated or saturated aliphatic chain. The aliphatic may be substituted with at least one (e.g., about 1 to about 5 or about 1 to about 3) heteroatoms (e.g., O, N, or S). In a particular embodiment, R is the residue (that portion of the fatty acid not including the ester end-group) alkyl chain of a fatty acid (saturated or unsaturated). In a particular embodiment, the fatty acid is unsaturated. Examples of fatty acids include, without limitation: caprylic acid, capric acid, lauric acid, myristic acid, palmitic acid, stearic acid, arachidic acid, behenic acid, myristoleic acid, palmitoleic acid, sapienic acid, oleic acid, elaidic acid, vaccenic acid, linoleic acid, linoelaidic acid, α-linolenic acid, arachidonic to acid, eicosapentaenoic acid, erucic acid, and docosahexaenoic acid. In a particular embodiment, the fatty acid is myristic acid.

Methods of synthesizing hydrophobic integrase inhibitor prodrugs are encompassed by the instant invention. In a particular embodiment, the integrase inhibitor prodrugs are synthesized through the conjugation of a hydrophobic group such as an aliphatic or alkyl group (e.g., a fatty acid) to the integrase inhibitor, optionally via a linker (e.g., a carbonyl group). In a particular embodiment, the hydrophobic group is conjugated to the integrase inhibitor via an —OH group (e.g., via an acylation reaction). In a particular embodiment, the hydrophobic group is conjugated through direct conjugation with a fatty acid under acidic conditions or through a group protection and deprotection method. Provided below is a scheme illustrating a method for synthesizing an integrase inhibitor prodrug (DTG (Scheme 1) and CAB (Scheme 2) prodrugs are exemplified, but similar methods can be employed for other integrase inhibitors) of the instant invention. The reagents, solvents and reaction conditions are illustrative.

Scheme 1

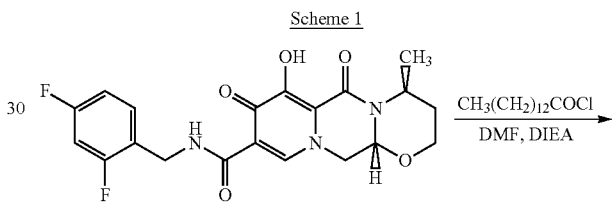

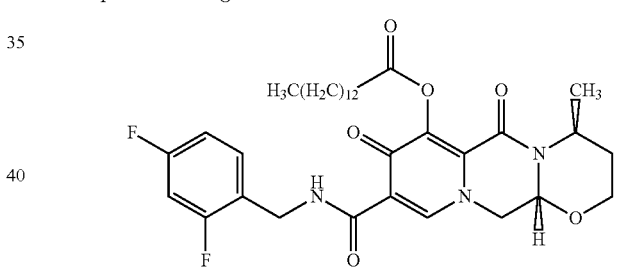

Scheme 2

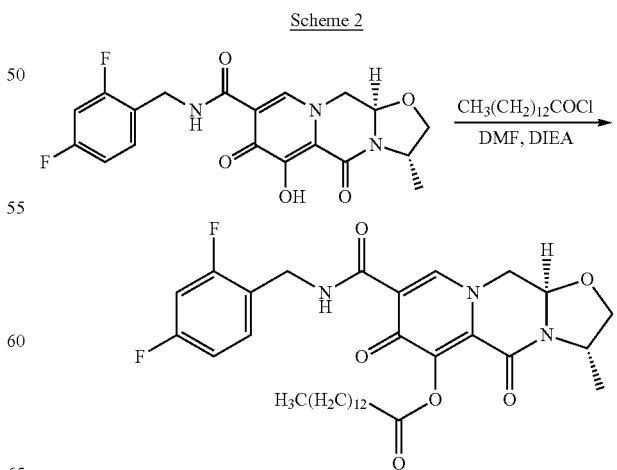

Scheme 3

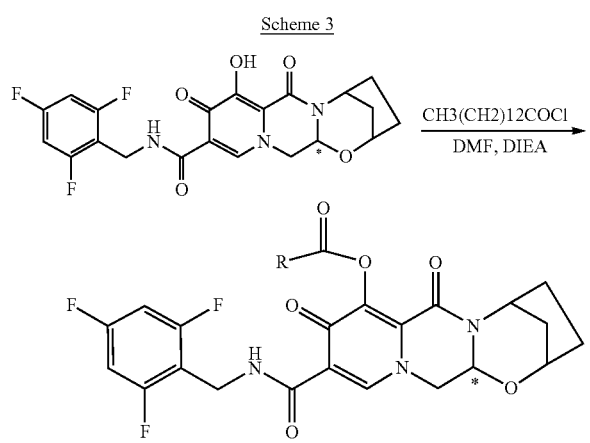

In a particular embodiment, integrase inhibitor prodrugs can be prepared according to the following steps: 1) deprotonation of the phenol functional group with a base (e.g., N,N diisopropylethylamine) and 2) reaction with acyl halide (e.g., chloride) or activated carboxylic acid (e.g., of a fatty acid). Steps 1 and 2 reactions may be performed in a single vessel. In a particular embodiment, the hydroxyl group may be deprotonated using the appropriate reagent (e.g., a base such as N,N diisopropylethylamine) and the alcohol anion may then be coupled with an acyl chloride or activated carboxylic acid to generate the prodrugs. Coupling reagents used to activate the carboxylic acid include, without limitation uranium salts, carbodiimide reagents, phosphonium salts and the like. The base may include, without limitation: triethylamine, N, N-diisopropylethylamine, collidine, etc. Polar aprotic solvents (e.g., without limitation, N,N-dimethylformamide, tetrahydrofuran and acetonitrile) may be used in the coupling reaction. The reagents may be mixed at about 0° C. and gradually warmed to temperature (e.g., room temperature) (e.g., over about 12-24 hours). The final compounds may be purified on a silica column chromatography and characterized by nuclear magnetic resonance spectroscopy and high performance liquid chromatography in tandem with mass spectrometry.

The methods for synthesizing the integrase inhibitor prodrugs may further comprise protection of other functional groups (e.g., amine and hydroxyl groups) to control chemoselectivity of the reaction. The method may further comprise deprotection after reacting the hydrophobic group with the integrase inhibitor to generate the desired compound. Hydroxyl-protecting groups include, without limitation, esters, acetyls, and ethers such as base sensitive groups like t-butyldimethylsilyl chloride (TBDMS-Cl) and t-butyldiphenylsilyl chloride. Other hydroxyl-protecting groups include, without limitation, phenylmethyl ether, trimethylsilyl ether, methoxymethyl ether, tetrahydropyranyl ether, t-butyl ether, allyl ether, benzyl ether, acetic acid ester, pivalic acid ester, and benzoic acid ester. The base used in this step may include amines such as, without limitation: pyridine, triethylamine, 4-dimethylaminopyridine, etc. Polar aprotic solvents such as N, N-dimethyl formamide and tetrahydrofuran may be used to run the reaction. The reagents can be mixed at 0° C. and gradually warmed to temperature over time (e.g., 4-24 hours). The hydroxyl-protected compounds can be purified by conventional methods such as column chromatography.

The instant invention also encompasses nanoparticles (sometimes referred to herein as nanoformulations) for the delivery of compounds to a cell. In a particular embodiment, the nanoparticle is for the delivery of antiretroviral therapy to a subject. The nanoparticles of the instant invention comprise at least one integrase inhibitor prodrug and at least one surfactant. In a particular embodiment, the nanoparticles comprise a spectroscopic-defined drug:surfactant (polymer) ratio that maintains optimal targeting of the drug nanoparticle to maintain a macrophage depot. In a particular embodiment, the drug:surfactant ratio (by weight) is from about 10:6 to about 1000:6, about 20:6 to about 500:6, about 50:6 to about 200:6, or about 100:6. These components of the nanoparticle, along with other optional components, are described hereinbelow.

Methods of synthesizing the nanoparticles of the instant invention are known in the art. In a particular embodiment, the methods generate nanoparticles comprising the prodrug (e.g., crystalline or amorphous) coated (either partially or completely) with a surfactant. Examples of synthesis methods include, without limitation, milling (e.g., wet milling), homogenization (e.g., high pressure homogenization), particle replication in nonwetting template (PRINT) technology, and/or sonication techniques. For example, U.S. Patent Application Publication No. 2013/0236553, incorporated by reference herein, provides methods suitable for synthesizing nanoparticles of the instant invention. In a particular embodiment, the surfactants are firstly chemically modified with targeting ligands and then used directly or mixed with non-targeted surfactants in certain molar ratios to coat on the surface of drug suspensions—e.g., by using a nanoparticle synthesis process (e.g., a crystalline nanoparticle synthesis process) such as milling (e.g., wet milling), homogenization (e.g., high pressure homogenization), particle replication in nonwetting template (PRINT) technology, and/or sonication techniques, thereby preparing targeted nanoformulations. The nanoparticles may be used with or without further purification, although the avoidance of further purification is desirable for quicker production of the nanoparticles. In a particular embodiment, the nanoparticles are synthesized using milling and/or homogenization. Targeted nanoparticles (e.g., using ligands with high molecular weight) may be developed through either physically or chemically coating and/or binding on the surface of surfactants and/or drug nanosuspensions.

The nanoparticles of the instant invention may be used to deliver at least one prodrug of the instant invention to a cell or a subject (including non-human animals). In a particular embodiment, the nanoparticles of the instant invention comprise at least two therapeutic agents, particularly wherein at least one is a prodrug of the instant invention. For example, the nanoparticle may comprise an integrase inhibitor prodrug of the instant invention and at least one other therapeutic agent (e.g., an anti-HIV agent). The nanoparticle may comprise a DTG prodrug of the instant invention and at least one other therapeutic agent (e.g., an anti-HIV agent). The nanoparticle may comprise a CAB prodrug of the instant invention and at least one other therapeutic agent (e.g., an anti-HIV agent). The nanoparticle may comprise a BIC prodrug of the instant invention and at least one other therapeutic agent (e.g., an anti-HIV agent). The nanoparticle may comprise a CAB prodrug of the instant invention, a DTG produg of the instant invention, and, optionally, at least one other therapeutic agent (e.g., an anti-HIV agent).

In a particular embodiment, the nanoparticles are a submicron colloidal dispersion of nanosized drug crystals (e.g., of prodrug) stabilized by surfactants (e.g., surfactant-coated drug crystals; a nanoformulation). In a particular embodiment, the nanoparticles (or the therapeutic agent (e.g., prodrug) of the nanoparticles) may be crystalline (solids having the characteristics of crystals), amorphous, or are solid-state nanoparticles of the therapeutic agent (e.g., prodrug) that is formed as crystal that combines the therapeutic agent (e.g., prodrug) and surfactant. As used herein, the term "crystalline" refers to an ordered state (i.e., non-amorphous) and/or a substance exhibiting long-range order in three dimensions. In a particular embodiment, the majority (e.g., at least 50%, 60%, 70%, 80%, 90%, 95% or more) of the therapeutic agent (and, optionally the hydrophobic portion of the surfactant) are crystalline.

In a particular embodiment, the nanoparticles are synthesized by adding the therapeutic agent (e.g., prodrug, optionally in free base form) to a surfactant (described below) solution and then generating the nanoparticles (e.g., by wet milling or high pressure homogenization). The prodrug and surfactant solution may be agitated prior the wet milling or high pressure homogenization.

In a particular embodiment, the resultant nanoparticle is up to about 2 or 3 µm in diameter (e.g., z-average diameter) or its longest dimension, particularly up to about 1 µm (e.g., about 100 nm to about 1 µm). For example, the diameter or longest dimension of the nanoparticle may be about 50 to about 800 nm. In a particular embodiment, the diameter or longest dimension of the nanoparticle is about 50 to about 750 nm, about 50 to about 500 nm, about 200 nm to about 500 nm, or about 200 nm to about 400 nm. The nanoparticles may be, for example, rod shaped, elongated rods, irregular, or round shaped. The nanoparticles of the instant invention may be neutral or charged. The nanoparticles may be charged positively or negatively.

An anti-HIV compound or an anti-HIV agent is a compound which inhibits HIV. The anti-HIV compound may be in produg form. Examples of additional anti-HIV agents that may be used in combination with the prodrugs of the invention include, without limitation:

(I) Nucleoside-analog reverse transcriptase inhibitors (NRTIs). NRTIs refer to nucleosides and nucleotides and analogues thereof that inhibit the activity of reverse transcriptase, particularly HIV-1 reverse trnscriptase. NRTIs comprise a sugar and base. Examples of nucleoside-analog reverse transcriptase inhibitors include, without limitation, adefovir dipivoxil, adefovir, lamivudine (e.g., the prodrug described in PCT/US15/54826), telbivudine, entecavir, tenofovir, stavudine, abacavir (e.g., the prodrug described in PCT/US15/54826), didanosine, emtricitabine, zalcitabine, and zidovudine.

(II) Non-nucleoside reverse transcriptase inhibitors (NNRTIs). NNRTIs are allosteric inhibitors which bind reversibly at a nonsubstrate-binding site on reverse transcriptase, particularly the HIV reverse transcriptase, thereby altering the shape of the active site or blocking polymerase activity. Examples of NNRTIs include, without limitation, delavirdine (BHAP, U-90152; RESCRIPTOR®), efavirenz (DMP-266, SUSTIVA®), nevirapine (VIRAMUNE®), PNU-142721, capravirine (S-1153, AG-1549), emivirine (+)-calanolide A (NSC-675451) and B, etravirine (TMC-125), rilpivirne (TMC278, Edurant™), DAPY (TMC120), BILR-355 BS, PHI-236, and PHI-443 (TMC-278).

(III) Protease inhibitors (PI). Protease inhibitors are inhibitors of a viral protease, particularly the HIV-1 protease. Examples of protease inhibitors include, without limitation, darunavir, amprenavir (141W94, AGENERASE®), tipranivir (PNU-140690, APTIVUS®), indinavir (MK-639; CRIXIVAN®), saquinavir (INVIRASE®, FORTOVASE®), fosamprenavir (LEXIVA®), lopinavir (ABT-378), ritonavir (ABT-538, NORVIR®), atazanavir (REYATAZ®), nelfinavir (AG-1343, VIRACEPT®), lasinavir (BMS-234475/CGP-61755), BMS-2322623, GW-640385X (VX-385), AG-001859, and SM-309515.

(IV) Fusion or entry inhibitors. Fusion or entry inhibitors are compounds, such as peptides, which block HIV entry into a cell (e.g., by binding to HIV envelope protein and blocking the structural changes necessary for the virus to fuse with the host cell). Examples of fusion inhibitors include, without limitation, CCR5 receptor antagonists (e.g., maraviroc (Selzentry®, Celsentri)), enfuvirtide (INN, FUZEON®), T-20 (DP-178, FUZEON®) and T-1249.

(V) Integrase inhibitors. Integrase inhibitors are a class of antiretroviral drug designed to block the action of integrase (e.g., HIV integrase), a viral enzyme that inserts the viral genome into the DNA of the host cell. Examples of integrase inhibitors include, without limitation, raltegravir, elvitegravir, and MK-2048.

Anti-HIV compounds also include maturation inhibitors (e.g., bevirimat). Maturation inhibitors are typically compounds which bind HIV gag and disrupt its processing during the maturation of the virus. Anti-HIV compounds also include HIV vaccines such as, without limitation, ALVAC® HIV (vCP1521), AIDSVAX® B/E (gp120), and combinations thereof. Anti-HIV compounds also include HIV antibodies (e.g., antibodies against gp120 or gp41), particularly broadly neutralizing antibodies.

More than one anti-HIV agent may be used, particularly where the agents have different mechanisms of action (as outlined above). For example, anti-HIV agents which are not integrase inhibitors may be combined with the integrase inhibitor prodrugs of the instant invention. The other anti-HIV agents may be administered concurrently and/or separately with the integrase inhibitor prodrugs of the instant invention. As explained above, the other anti-HIV agents may be formulated with the integrase inhibitor prodrugs in the nanoparticles of the instant invention. The other anti-HIV agents may be contained within a composition (e.g., a pharmaceutical composition comprising at least one pharmaceutically acceptable carrier) with the integrase inhibitor prodrugs (and/or nanoformulations thereof) of the instant invention. The other anti-HIV agents may be administered separately (e.g., in a composition (e.g., a pharmaceutical composition comprising at least one pharmaceutically acceptable carrier)) from the integrase inhibitor prodrugs of the instant invention.

Specific combinations with the integrase inhibitor prodrugs of the instant invention include, without limitation: integrase inhibitor prodrug with rilpivirine, integrase inhibitor prodrug with lamivudine, integrase inhibitor prodrug with lamivudine prodrug (e.g., the lamivudine prodrug described in PCT/US15/54826), integrase inhibitor prodrug with lamivudine and abacavir, integrase inhibitor prodrug with lamivudine and abacavir prodrug (e.g., the abacavir prodrug described in PCT/US15/54826), integrase inhibitor prodrug with lamivudine prodrug (e.g., the lamivudine prodrug described in PCT/US15/54826) and abacavir, integrase inhibitor prodrug with lamivudine prodrug (e.g., the lamivudine prodrug described in PCT/US15/54826) and abacavir prodrug (e.g., the abacavir prodrug described in PCT/US15/54826), DTG prodrug with rilpivirine, DTG prodrug with lamivudine, DTG prodrug with lamivudine prodrug (e.g., the lamivudine prodrug described in PCT/US15/54826), DTG prodrug with lamivudine and abacavir, DTG prodrug with lamivudine and abacavir prodrug (e.g., the abacavir prodrug described in PCT/US15/54826), DTG prodrug with lamivudine prodrug (e.g., the lamivudine prodrug described in PCT/US15/54826) and abacavir, DTG prodrug with lamivudine prodrug (e.g., the lamivudine prodrug described in PCT/US15/54826) and abacavir prodrug (e.g., the abacavir prodrug described in PCT/US15/54826), CAB prodrug with rilpivirine, CAB prodrug with lamivudine, CAB prodrug with lamivudine prodrug (e.g., the lamivudine prodrug described in PCT/US15/54826), CAB prodrug with lamivudine and abacavir, CAB prodrug with lamivudine and abacavir prodrug (e.g., the abacavir prodrug described in PCT/US15/54826), CAB prodrug with lamivudine prodrug (e.g., the lamivudine prodrug described in PCT/US15/54826) and abacavir, and CAB prodrug with lamivudine prodrug (e.g., the lamivudine prodrug described in PCT/US15/54826) and abacavir prodrug (e.g., the abacavir prodrug described in PCT/US15/54826). As explained above, the other anti-HIV agents may be administered concurrently and/or separately with the integrase inhibitor prodrugs of the instant invention. The other anti-HIV agents may be formulated with the integrase inhibitor prodrugs in the nanoparticles of the instant invention. The other anti-HIV agents may be contained within a composition (e.g., a pharmaceutical composition comprising at least one pharmaceutically acceptable carrier) with the integrase inhibitor prodrugs (and/or nanoformulations thereof) of the instant invention. The other anti-HIV agents may be administered separately (e.g., in a composition (e.g., a pharmaceutical composition comprising at least one pharmaceutically acceptable carrier)) from the integrase inhibitor prodrugs of the instant invention.

In a particular embodiment, the anti-HIV therapy is highly active antiretroviral therapy (HAART). In a particular embodiment, at least two NRTIs and one NNRTI are administered along with the integrase inhibitor prodrugs of the instant invention, optionally with at least one protease inhibitor and/or other anti-HIV agent.

As stated hereinabove, the nanoparticles of the instant invention comprise at least one surfactant. A "surfactant" refers to a surface-active agent, including substances commonly referred to as wetting agents, detergents, dispersing agents, or emulsifying agents. Surfactants are usually organic compounds that are amphiphilic.

Examples of surfactants include, without limitation, synthetic or natural phospholipids, PEGylated lipids (e.g., PEGylated phospholipid), lipid derivatives, polysorbates, amphiphilic copolymers, amphiphilic block copolymers, poly(ethylene glycol)-co-poly(lactide-co-glycolide) (PEG-PLGA), their derivatives, ligand-conjugated derivatives and combinations thereof. Other surfactants and their combinations that can form stable nanosuspensions and/or can chemically/physically bind to the targeting ligands of HIV infectable/infected CD4+ T cells, macrophages and dendritic cells can be used in the instant invention. Further examples of surfactants include, without limitation: 1) nonionic surfactants (e.g., pegylated and/or polysaccharide-conjugated polyesters and other hydrophobic polymeric blocks such as poly(lactide-co-glycolide) (PLGA), polylactic acid (PLA), polycaprolactone (PCL), other polyesters, poly(propylene oxide), poly(1,2-butylene oxide), poly(n-butylene oxide), poly(tetrahydrofurane), and poly(styrene); glyceryl esters, polyoxyethylene fatty alcohol ethers, polyoxyethylene sorbitan fatty acid esters, polyoxyethylene fatty acid esters, sorbitan esters, glycerol monostearate, polyethylene glycols, polypropyleneglycols, cetyl alcohol, cetostearyl alcohol, stearyl alcohol, aryl alkyl polyether alcohols, polyoxyethylene-polyoxypropylene copolymers, poloxamines, cellulose, methylcellulose, hydroxylmethylcellulose, hydroxypropylcellulose, hydroxypropylmethylcellulose, polysaccharides, starch and their derivatives, hydroxyethylstarch, polyvinyl alcohol (PVA), polyvinylpyrrolidone, and their combination thereof); and 2) ionic surfactants (e.g., phospholipids, amphiphilic lipids, 1,2-dialkylglycero-3-alkylphophocholines, 1, 2-distearoyl-sn-glecro-3-phosphocholine (DSPC), 1,2-distearoyl-sn-glycero-3-phosphoethanolamine-N-[carboxy(polyethylene glycol) (DSPE-PEG), dimethylaminoethanecarbamoyl cheolesterol (DC-Chol), N-[1-(2,3-Dioleoyloxy)propyl]-N,N,N-trimethylammonium (DOTAP), alkyl pyridinium halides, quaternary ammonium compounds, lauryldimethylbenzylammonium, acyl carnitine hydrochlorides, dimethyldioctadecylammonium (DDAB), n-octylamines, oleylamines, benzalkonium, cetyltrimethylammonium, chitosan, chitosan salts, poly(ethylenimine) (PEI), poly(N-isopropyl acrylamide) (PNIPAM), and poly (allylamine) (PAH), poly (dimethyldiallylammonium chloride) (PDDA), alkyl sulfonates, alkyl phosphates, alkyl phosphonates, potassium laurate, triethanolamine stearate, sodium lauryl sulfate, sodium dodecylsulfate, alkyl polyoxyethylene sulfates, alginic acid, alginic acid salts, hyaluronic acid, hyaluronic acid salts, gelatins, dioctyl sodium sulfosuccinate, sodium carboxymethylcellulose, cellulose sulfate, dextran sulfate and carboxymethylcellulose, chondroitin sulfate, heparin, synthetic poly(acrylic acid) (PAA), poly (methacrylic acid) (PMA), poly(vinyl sulfate) (PVS), poly(styrene sulfonate) (PSS), bile acids and their salts, cholic acid, deoxycholic acid, glycocholic acid, taurocholic acid, glycodeoxycholic acid, derivatives thereof, and combinations thereof).

In a particular embodiment of the invention, the surfactant is present in the nanoparticle and/or surfactant solution to synthesize the nanoparticle (as described hereinabove) at a concentration ranging from about 0.0001% to about 10% or 15% by weight. In a particular embodiment, the concentration of the surfactant ranges from about 0.01% to about 15%, about 0.01% to about 10%, or about 0.1% to about 6% by weight. In a particular embodiment, the nanoparticle comprises at least about 50%, 75%, 80%, 85%, 90%, 95%, 97%, 98%, 99% or higher therapeutic agent by weight.

The surfactant of the instant invention may be charged or neutral. In a particular embodiment, the surfactant is neutral or negatively charged (e.g., poloxamers, polysorbates, phospholipids, and their derivatives).

In a particular embodiment, the surfactant is an amphiphilic block copolymer or lipid derivative. In a particular, embodiment, at least one surfactant of the nanoparticle is an amphiphilic block copolymer, particularly a copolymer comprising at least one block of poly(oxyethylene) and at least one block of poly(oxypropylene). In a particular embodiment, the surfactant is a triblock amphiphilic block copolymer. In a particular embodiment, the surfactant is a triblock amphiphilic block copolymer comprising a central hydrophobic block of polypropylene glycol flanked by two hydrophilic blocks of polyethylene glycol. In a particular embodiment, the surfactant is poloxamer 407.

In a particular embodiment, the amphiphilic block copolymer is a copolymer comprising at least one block of poly(oxyethylene) and at least one block of poly(oxypropylene). Amphiphilic block copolymers are exemplified, without limitation, to by the block copolymers having the formulas:

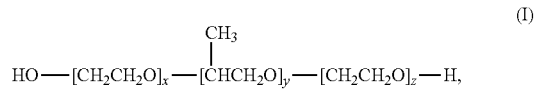

(I)

-continued

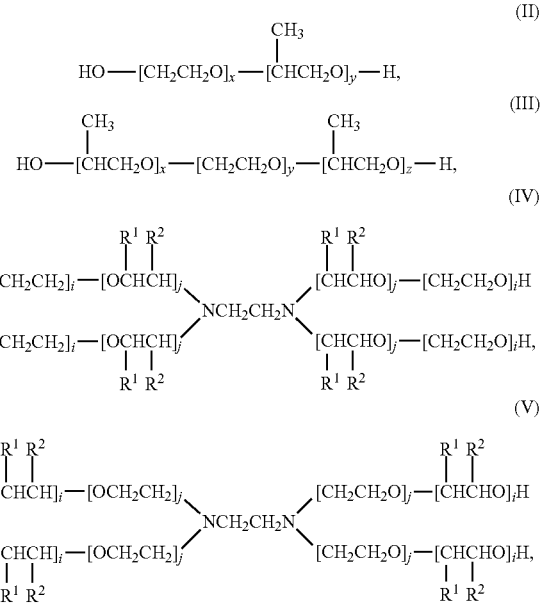

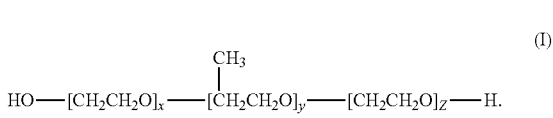

in which x, y, z, i, and j have values from about 2 to about 800, particularly from about 5 to about 200 or about 5 to about 80, and wherein for each $R^1$, $R^2$ pair, as shown in formula (IV) and (V), one is hydrogen and the other is a methyl group. The ordinarily skilled artisan will recognize that the values of x, y, and z will usually represent a statistical average and that the values of x and z are often, though not necessarily, the same. Formulas (I) through (III) are oversimplified in that, in practice, the orientation of the isopropylene radicals within the B block will be random. This random orientation is indicated in formulas (IV) and (V), which are more complete. Such poly(oxyethylene)-poly (oxypropylene) compounds have been described by Santon (Am. Perfumer Cosmet. (1958) 72(4):54-58); Schmolka (Loc. cit. (1967) 82(7):25-30), Schick, ed. (Non-ionic Suifactants, Dekker, N.Y., 1967 pp. 300-371). A number of such compounds are commercially available under such generic trade names as "lipoloxamers", "Pluronics®," "poloxamers," and "synperonics." Pluronic® copolymers within the B-A-B formula, as opposed to the A-B-A formula typical of Pluronics®, are often referred to as "reversed" Pluronics®, "Pluronic® R" or "meroxapol." Generally, block copolymers can be described in terms of having hydrophilic "A" and hydrophobic "B" block segments. Thus, for example, a copolymer of the formula A-B-A is a triblock copolymer consisting of a hydrophilic block connected to a hydrophobic block connected to another hydrophilic block. The "polyoxamine" polymer of formula (IV) is available from BASF under the tradename Tetronic®. The order of the polyoxyethylene and polyoxypropylene blocks represented in formula (IV) can be reversed, creating Tetronic R®, also available from BASF (see, Schmolka, J. Am. Oil. Soc. (1979) 59:110).

Polyoxypropylene-polyoxyethylene block copolymers can also be designed with hydrophilic blocks comprising a random mix of ethylene oxide and propylene oxide repeating units. To maintain the hydrophilic character of the block, ethylene oxide can predominate. Similarly, the hydrophobic block can be a mixture of ethylene oxide and propylene oxide repeating units. Such block copolymers are available from BASF under the tradename Pluradot™. Poly(oxyethylene)-poly(oxypropylene) block units making up the first segment need not consist solely of ethylene oxide. Nor is it necessary that all of the B-type segment consist solely of propylene oxide units. Instead, in the simplest cases, for example, at least one of the monomers in segment A may be substituted with a side chain group.

A number of poloxamer copolymers are designed to meet the following formula:

$$\text{HO}-[\text{CH}_2\text{CH}_2\text{O}]_x-[\overset{\overset{\displaystyle CH_3}{|}}{\text{CH}}\text{CH}_2\text{O}]_y-[\text{CH}_2\text{CH}_2\text{O}]_Z-\text{H}. \quad (I)$$

Examples of poloxamers include, without limitation, Pluronic® L31, L35, F38, L42, L43, L44, L61, L62, L63, L64, P65, F68, L72, P75, F77, L81, P84, P85, F87, F88, L92, F98, L101, P103, P104, P105, F108, L121, L122, L123, F127, 10R5, 10R8, 12R3, 17R1, 17R2, 17R4, 17R8, 22R4, 25R1, 25R2, 25R4, 25R5, 25R8, 31R1, 31R2, and 31R4. Pluronic® block copolymers are designated by a letter prefix followed by a two or a three digit number. The letter prefixes (L, P, or F) refer to the physical form of each polymer, (liquid, paste, or flakeable solid). The numeric code defines the structural parameters of the block copolymer. The last digit of this code approximates the weight content of EO block in tens of weight percent (for example, 80% weight if the digit is 8, or 10% weight if the digit is 1). The remaining first one or two digits encode the molecular mass of the central PO block. To decipher the code, one should multiply the corresponding number by 300 to obtain the approximate molecular mass in daltons (Da). Therefore Pluronic® nomenclature provides a convenient approach to estimate the characteristics of the block copolymer in the absence of reference literature. For example, the code 'F127' defines the block copolymer, which is a solid, has a PO block of 3600 Da (12×300) and 70% weight of EO. The precise molecular characteristics of each Pluronic® block copolymer can be obtained from the manufacturer.

Other biocompatible amphiphilic copolymers include those described in Gaucher et al. (J. Control Rel. (2005) 109:169-188. Examples of other polymers include, without limitation, poly(2-oxazoline) amphiphilic block copolymers, polyethylene glycol-polylactic acid (PEG-PLA), PEG-PLA-PEG, polyethylene glycol-poly(lactide-co-glycolide) (PEG-PLG), polyethylene glycol-poly(lactic-co-glycolic acid) (PEG-PLGA), polyethylene glycol-polycaprolactone (PEG-PCL), polyethylene glycol-polyaspartate (PEG-PAsp), polyethylene glycol-poly(glutamic acid) (PEG-PGlu), polyethylene glycol-poly(acrylic acid) (PEG-PAA), polyethylene glycol-poly(methacrylic acid) (PEG-PMA), polyethylene glycol-poly(ethyleneimine) (PEG-PEI), polyethylene glycol-poly(L-lysine) (PEG-PLys), polyethylene glycol-poly(2-(N,N-dimethylamino)ethyl methacrylate) (PEG-PDMAEMA), polyethylene glycol-chitosan, and derivatives thereof.

In a particular embodiment, the surfactant is poloxamer 407 (Pluronic® F127).

The surfactant of the instant invention may be linked to a targeting ligand. A targeting ligand is a compound that specifically binds to a specific type of tissue or cell type (e.g., in a desired target:cell ratio). For example, a targeting ligand may be used for engagement or binding of a target cell (e.g., a macrophage) surface marker or receptor which may facilitate its uptake into the cell (e.g., within a protected subcellular organelle that is free from metabolic degradation). In a particular embodiment, the targeting ligand is a ligand for a cell surface marker/receptor. The targeting ligand may be an antibody or fragment thereof immunologically specific for a cell surface marker (e.g., protein or carbohydrate) preferentially or exclusively expressed on the targeted tissue or cell type. Targeting ligands (e.g., folic acid) may be conjugated to the polymer by methods known in the art (e.g., PCT/US15/54826). The targeting ligand may be linked directly to the surfactant or via a linker. Generally, the linker is a chemical moiety comprising a covalent bond or a chain of atoms that covalently attaches the ligand to the surfactant. The linker can be linked to any synthetically feasible position of the ligand and the surfactant. Exemplary linkers may comprise at least one optionally substituted; saturated or unsaturated; linear, branched or cyclic aliphatic group, an alkyl group, or an optionally substituted aryl group. The linker may be a lower alkyl or aliphatic. The linker may also be a polypeptide (e.g., from about 1 to about 10 amino acids, particularly about 1 to about 5). In a particular embodiment, the targeting moiety is linked to either of both ends of the surfactant. The linker may be non-degradable and may be a covalent bond or any other chemical structure which cannot be substantially cleaved or cleaved at all under physiological environments or conditions.

The nanoparticles/nanoformulations of the instant invention may comprise targeted and/or non-targeted surfactants. In a particular embodiment, the molar ratio of targeted and non-targeted surfactants in the nanoparticles/nanoformulations of the instant invention is from about 0.001 to 100%, about 1% to about 99%, about 5% to about 95%, about 10% to about 90%, about 25% to about 75%, about 30% to about 60%, or about 40%. In a particular embodiment, the nanoparticle comprises only targeted surfactants. In a particular embodiment, the nanoparticles/nanoformulations of the instant invention comprise a folate targeted surfactant and a non-targeted version of the surfactant. In a particular embodiment, the nanoparticles/nanoformulations of the instant invention comprise folate-poloxamer 407 (FA-P407) and/or poloxamer 407.

The targeted nanoformulations of the instant invention may comprise a targeting ligand for directing the nanoparticles to HIV tissue and cellular sanctuaries/reservoirs (e.g., central nervous system, gut associated lymphoid tissues (GALT), CD4+ T cells, macrophages, dendritic cells, etc.). In a particular embodiment, the targeting ligand is a macrophage targeting ligand; CD4+ T cell targeting ligand, or a dendritic cell targeting ligand. Macrophage targeting ligands include, without limitation, folate receptor ligands (e.g., folate (folic acid) and folate receptor antibodies and fragments thereof (see, e.g., Sudimack et al. (2000) Adv. Drug Del. Rev., 41:147-162)), mannose receptor ligands (e.g., mannose), formyl peptide receptor (FPR) ligands (e.g., N-formyl-Met-Leu-Phe (fMLF)), and tuftsin (the tetrapeptide Thr-Lys-Pro-Arg). Other targeting ligands (e.g., for targeting HIV reservoirs) include, without limitation, hyaluronic acid, gp120 and peptide fragments thereof, and ligands or antibodies specific for CD4, CCR5, CXCR4, CD7, CD111, CD204, CD49a, or CD29. As demonstrated hereinbelow, the targeting of the nanoparticles (e.g., to macrophage) provides for superior targeting, decreased excretion rates, decreased toxicity, and prolonged half life compared to free drug or non-targeted nanoparticles.

The instant invention encompasses pharmaceutical compositions comprising at least one prodrug and/or nanoparticle of the instant invention (sometimes referred to herein as nanoART) and at least one pharmaceutically acceptable carrier. As stated hereinabove, the prodrugs and/or nanoparticles may comprise more than one therapeutic agent. In a particular embodiment, the pharmaceutical composition comprises a first prodrugs and/or nanoparticles comprising a first therapeutic agent(s) and a second nanoparticle comprising a second therapeutic agent(s), wherein the first and second therapeutic agents are different. The pharmaceutical compositions of the instant invention may further comprise other therapeutic agents (e.g., other anti-HIV compounds (e.g., those described herein)).

The present invention also encompasses methods for preventing, inhibiting, and/or treating a viral infection, particularly retroviral or lentiviral infections, particularly HIV infections (e.g., HIV-1). The pharmaceutical compositions of the instant invention can be administered to an animal, in particular a mammal, more particularly a human, in order to treat/inhibit an HIV infection. The pharmaceutical compositions of the instant invention may also comprise at least one other antiviral agent, particularly at least one other anti-HIV compound/agent. The additional anti-HIV compound may also be administered in a separate pharmaceutical composition from the anti-HIV NPs of the instant invention. The pharmaceutical compositions may be administered at the same time or at different times (e.g., sequentially).

The dosage ranges for the administration of the pharmaceutical compositions of the invention are those large enough to produce the desired effect (e.g., curing, relieving, treating, and/or preventing the HIV infection, the symptoms of it (e.g., AIDS, ARC), or the predisposition towards it). In a particular embodiment, the pharmaceutical composition of the instant invention is administered to the subject at an amount from about 5 µg/kg to about 500 mg/kg. In a particular embodiment, the pharmaceutical composition of the instant invention is administered to the subject at an amount greater than about 5 µg/kg, greater than about 50 µg/kg, greater than about 0.1 mg/kg, greater than about 0.5 mg/kg, greater than about 1 mg/kg, or greater than about 5 mg/kg. In a particular embodiment, the pharmaceutical composition of the instant invention is administered to the subject at an amount from about 0.5 mg/kg to about 100 mg/kg, about 10 mg/kg to about 100 mg/kg, or about 15 mg/kg to about 50 mg/kg. The dosage should not be so large as to cause significant adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications.

The prodrugs and/or nanoparticles described herein will generally be administered to a patient as a pharmaceutical composition. The term "patient" as used herein refers to human or animal subjects. These nanoparticles may be employed therapeutically, under the guidance of a physician.

The pharmaceutical compositions comprising the prodrugs and/or nanoparticles of the instant invention may be conveniently formulated for administration with any pharmaceutically acceptable carrier(s). For example, the complexes may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents, or suitable mixtures thereof, particularly an aqueous solution. The concentration of the nanoparticles in the chosen medium may be varied and the medium may be chosen based on the desired route of administration of the pharmaceutical composition. Except insofar as any conventional media or agent is incompatible with the nanoparticles to be administered, its use in the pharmaceutical composition is contemplated.

The dose and dosage regimen of prodrugs and/or nanoparticles according to the invention that are suitable for administration to a particular patient may be determined by a physician considering the patient's age, sex, weight, general medical condition, and the specific condition for which the prodrugs and/or nanoparticles are being administered and the severity thereof. The physician may also take into account the route of administration, the pharmaceutical carrier, and the prodrugs and/or nanoparticles's biological activity.

Selection of a suitable pharmaceutical composition will also depend upon the mode of administration chosen. For example, the prodrugs and/or nanoparticles of the invention may be administered by direct injection or intravenously. In this instance, a pharmaceutical composition comprises the prodrugs and/or nanoparticles dispersed in a medium that is compatible with the site of injection.

Prodrugs and/or nanoparticles of the instant invention may be administered by any method. For example, the prodrugs and/or nanoparticles of the instant invention can be administered, without limitation parenterally, subcutaneously, orally, topically, pulmonarily, rectally, vaginally, intravenously, intraperitoneally, intrathecally, intracerbrally, epidurally, intramuscularly, intradermally, or intracarotidly. In a particular embodiment, the nanoparticles are administered intramuscularly, subcutaneously, or to the bloodstream (e.g., intravenously). Pharmaceutical compositions for injection are known in the art. If injection is selected as a method for administering the nanoparticle, steps must be taken to ensure that sufficient amounts of the molecules or cells reach their target cells to exert a biological effect. Dosage forms for oral administration include, without limitation, tablets (e.g., coated and uncoated, chewable), gelatin capsules (e.g., soft or hard), lozenges, troches, solutions, emulsions, suspensions, syrups, elixirs, powders/granules (e.g., reconstitutable or dispersible) gums, and effervescent tablets. Dosage forms for parenteral administration include, without limitation, solutions, emulsions, suspensions, dispersions and powders/granules for reconstitution. Dosage forms for topical administration include, without limitation, creams, gels, ointments, salves, patches and transdermal delivery systems.

Pharmaceutical compositions containing a prodrug and/or nanoparticle of the present invention as the active ingredient in intimate admixture with a pharmaceutically acceptable carrier can be prepared according to conventional pharmaceutical compounding techniques. The carrier may take a wide variety of forms depending on the form of pharmaceutical composition desired for administration, e.g., intravenous, oral, direct injection, intracranial, and intravitreal.

A pharmaceutical composition of the invention may be formulated in dosage unit form for ease of administration and uniformity of dosage. Dosage unit form, as used herein, refers to a physically discrete unit of the pharmaceutical composition appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. In a particular embodiment, the nanoformulations of the instant invention, due to their long-acting therapeutic effect, may be administered once every 1 to 12 months or even less frequently. For example, the nanoformulations of the instant invention may be administered once every 0.5, 1, 2, 3, 4, 5, 6, 7, 8, 9, 10, 11, 12, 15, 18, 21, 24, or more months.

Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of prodrugs and/or nanoparticles may be determined by evaluating the toxicity of the molecules or cells in animal models. Various concentrations of nanoparticles in pharmaceutical composition may be administered to mice, and the minimal and maximal dosages may be determined based on the beneficial results and side effects observed as a result of the treatment. Appropriate dosage unit may also be determined by assessing the efficacy of the prodrug and/or nanoparticle treatment in combination with other standard drugs. The dosage units of nanoparticle may be determined individually or in combination with each treatment according to the effect detected.

The pharmaceutical composition comprising the prodrugs and/or nanoparticles may be administered at appropriate intervals until the pathological symptoms are reduced or alleviated, after which the dosage may be reduced to a maintenance level. The appropriate interval in a particular case would normally depend on the condition of the patient.

The instant invention encompasses methods of treating a disease/disorder comprising administering to a subject in need thereof a pharmaceutical composition comprising a prodrug and/or nanoparticle of the instant invention and, preferably, at least one pharmaceutically acceptable carrier. The instant invention also encompasses methods wherein the subject is treated via ex vivo therapy. In particular, the method comprises removing cells from the subject, exposing/contacting the cells in vitro to the nanoparticles of the instant invention, and returning the cells to the subject. In a particular embodiment, the cells comprise macrophage. Other methods of treating the disease or disorder may be combined with the methods of the instant invention may be co-administered with the pharmaceutical compositions of the instant invention.

The instant also encompasses delivering the nanoparticle of the instant invention to a cell in vitro (e.g., in culture). The prodrugs and/or nanoparticles may be delivered to the cell in at least one carrier.

Definitions

The following definitions are provided to facilitate an understanding of the present invention.

The singular forms "a," "an," and "the" include plural referents unless the context clearly dictates otherwise.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in "Remington's Pharmaceutical Sciences" by E.W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

The term "treat" as used herein refers to any type of treatment that imparts a benefit to a patient afflicted with a disease, including improvement in the condition of the patient (e.g., in one or more symptoms), delay in the progression of the condition, etc. In a particular embodiment, the treatment of a retroviral infection results in at least an inhibition/reduction in the number of infected cells and/or detectable viral levels.

As used herein, the term "prevent" refers to the prophylactic treatment of a subject who is at risk of developing a condition (e.g., HIV infection) resulting in a decrease in the probability that the subject will develop the condition.

A "therapeutically effective amount" of a compound or a pharmaceutical composition refers to an amount effective to prevent, inhibit, treat, or lessen the symptoms of a particular disorder or disease. The treatment of a microbial infection (e.g., HIV infection) herein may refer to curing, relieving, and/or preventing the microbial infection, the symptom(s) of it, or the predisposition towards it.

As used herein, the term "therapeutic agent" refers to a chemical compound or biological molecule including, without limitation, nucleic acids, peptides, proteins, and antibodies that can be used to treat a condition, disease, or disorder or reduce the symptoms of the condition, disease, or disorder.

As used herein, the term "small molecule" refers to a substance or compound that has a relatively low molecular weight (e.g., less than 4,000, less than 2,000, particularly less than 1 kDa or 800 Da). Typically, small molecules are organic, but are not proteins, polypeptides, or nucleic acids, though they may be amino acids or dipeptides.

The term "antimicrobials" as used herein indicates a substance that kills or inhibits the growth of microorganisms such as bacteria, fungi, viruses, or protozoans.

As used herein, the term "antiviral" refers to a substance that destroys a virus and/or suppresses replication (reproduction) of the virus. For example, an antiviral may inhibit and or prevent: production of viral particles, maturation of viral particles, viral attachment, viral uptake into cells, viral assembly, viral release/budding, viral integration, etc.

As used herein, the term "highly active antiretroviral therapy" (HAART) refers to HIV therapy with various combinations of therapeutics such as nucleoside reverse transcriptase inhibitors, non-nucleoside reverse transcriptase inhibitors, HIV protease inhibitors, and fusion inhibitors.

As used herein, the term "amphiphilic" means the ability to dissolve in both water and lipids/apolar environments. Typically, an amphiphilic compound comprises a hydrophilic portion and a hydrophobic portion. "Hydrophobic" designates a preference for apolar environments (e.g., a hydrophobic substance or moiety is more readily dissolved in or wetted by non-polar solvents, such as hydrocarbons, than by water). "Hydrophobic" compounds are, for the most part, insoluble in water. As used herein, the term "hydrophilic" means the ability to dissolve in water.

As used herein, the term "polymer" denotes molecules formed from the chemical union of two or more repeating units or monomers. The term "block copolymer" most simply refers to conjugates of at least two different polymer segments, wherein each polymer segment comprises two or more adjacent units of the same kind.

An "antibody" or "antibody molecule" is any immunoglobulin, including antibodies and fragments thereof (e.g., scFv), that binds to a specific antigen. As used herein, antibody or antibody molecule contemplates intact immunoglobulin molecules, immunologically active portions of an immunoglobulin molecule, and fusions of immunologically active portions of an immunoglobulin molecule.

As used herein, the term "immunologically specific" refers to proteins/polypeptides, particularly antibodies, that bind to one or more epitopes of a protein or compound of interest, but which do not substantially recognize and bind other molecules in a sample containing a mixed population of antigenic biological molecules.

As used herein, the term "targeting ligand" refers to any compound which specifically binds to a specific type of tissue or cell type, particularly without substantially binding other types of tissues or cell types. Examples of targeting ligands include, without limitation: proteins, polypeptides, peptides, antibodies, antibody fragments, hormones, ligands, carbohydrates, steroids, nucleic acid molecules, and polynucleotides.

The term "aliphatic" refers to a non-aromatic hydrocarbon-based moiety. Aliphatic compounds can be acyclic (e.g., linear or branched) or cyclic moieties (e.g., alkyl and cycloalkyl) and can be saturated or unsaturated (e.g., alkyl, alkenyl, and alkynyl). Aliphatic compounds may comprise a mostly carbon main chain (e.g., 1 to about 30 carbons) and comprise heteroatoms and/or substituents (see below). The term "alkyl", alone or in combination with any other term, refers to a straight-chain or branched-chain saturated aliphatic hydrocarbon radical containing the specified number of carbon atoms, preferably from 3-30 carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like. The hydrocarbon chain of the alkyl groups may optionally be interrupted with one or more heteroatom (e.g., oxygen, nitrogen, or sulfur). An alkyl (or aliphatic) may, optionally, be substituted (e.g. with fewer than about 8, fewer than about 6, or 1 to about 4 substituents). The term "lower alkyl" or "lower aliphatic" refers to an alkyl or aliphatic, respectively, which contains 1 to 3 carbons in the hydrocarbon chain. Alkyl or aliphatic substituents include, without limitation, alkyl (e.g., lower alkyl), alkenyl, halo (such as F, Cl, Br, I), haloalkyl (e.g., $CCl_3$ or $CF_3$), alkoxyl, alkylthio, hydroxy, methoxy, carboxyl, oxo, epoxy, alkyloxycarbonyl, alkylcarbonyloxy, amino, carbamoyl (e.g., $NH_2C(=O)-$ or $NHRC(=O)-$, wherein R is an alkyl), urea ($-NHCONH_2$), alkylurea, aryl, ether, ester, thioester, nitrile, nitro, amide, carbonyl, carboxylate and thiol. Aliphatic and alkyl groups having at least about 5 carbons in the main chain are generally hydrophobic, absent extensive substitutions with hydrophilic substituents.

"Linker" refers to a chemical moiety comprising a covalent bond or a chain of atoms that covalently attach at least two compounds. The linker can be linked to any synthetically feasible position of the compounds, but preferably in such a manner as to avoid blocking the compounds desired activity. Linkers are generally known in the art. In a particular embodiment, the linker may contain from 0 (i.e., a bond) to about 50 atoms, from 0 to about 10 atoms, or from about 1 to about 5 atoms. The linker may be biodegradable under physiological environments or conditions (e.g., comprise an ester bond).

The term "alkylene" or "alkenyl" refers to a straight or branched chain divalent hydrocarbon radical, preferably having from one to thirty carbon atoms wherein at least one pair of carbon atoms is connected by a double bond. Examples of "alkylene" as used herein include, but are not limited to, methylene, ethylene, propylene, butylene, isobutylene and the like.

The term "aryl" alone or in combination with any other term, refers to a carbocyclic aromatic moiety (such as phenyl or naphthyl) containing the specified number of carbon atoms, preferably from 6-10 carbon atoms. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like. Unless otherwise indicated, the term "aryl" also includes each possible positional isomer of an aromatic hydrocarbon radical, such as in 1-naphthyl, 2-naphthyl, 5-tetrahydronaphthyl, 6-tetrahydronaphthyl, 1-phenanthridinyl, 2-phenanthridinyl, 3-phenanthridinyl, 4-phenanthridinyl, 7-phenanthridinyl, 8-phenanthridinyl, 9-phenanthridinyl and 10-phenanthridinyl. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like.

As used herein, the term "cycloalkyl" refers to a saturated monocyclic carbocyclic ring having from 3 to 8 carbon atoms, unless a different number of atoms is specified. Cycloalkyl includes by way of example cyclopropyl, cyclobutyl, cyclopentyl, cyclohexyl, cycloheptyl and cyclooctyl. Preferred cycloalkyl groups include substituted and unsubstituted $C_{3-6}$cycloalkyl. The term cycloalkyl and variations thereof (i.e., "$C_{3-6}$cycloalkyl") is intended to independently describe each member of the genus. Likewise, "cycloalkenyl" refers to cyclized carbon chain having at least one alkenyl radical, preferably having 3 to 8 carbon atoms.

The following examples provide illustrative methods of practicing the instant invention, and they are not intended to limit the scope of the invention in any way.

EXAMPLE 1

Herein, a novel long acting dolutegravir (DTG) prodrug nanoformulation is provided with improved biological activity, extended drug half-life, increased hydrophobicity, improved protein binding capacity, improved biodistribution (tissue distribution), improved plasma half-life, and increased antiviral efficacy when compared to the parent drug. The developed hydrophobic modified DTG prodrug (MDTG) exhibits improved cellular uptake of up to 100-fold compared to native drug formulations. Similarly, significant enhancements in cellular retention and antiretroviral activities were seen. Of significance, the MDTG nanoformulations demonstrated an up to a 10-fold improvement in pharmacokinetics compared to native drug formulations. The injectable may be administered once/month or longer and maintain consistent drug concentration. As such, the instant prodrugs and formulations thereof will improve compliance, affect drug reservoir targeting and reduce systemic toxicities. The prodrugs are derivatives of DTG to conjugated to hydrophobic cleavable moieties. Here, the hydrophobic parent compound is converted into a more hydrophobic ester derivative. This is achieved through attachment of a fatty acid, alkyl or aryl moiety that can improve drug protein binding and bioavailability. The ester chemical bond linkage is susceptible to enzymatic cleavage. The derivatives possess improved hydrophobicity when compared to the parent drug. The "more" hydrophobic nature of the crystalline prodrugs improve nanoformulations by making them even more long acting with improved biopharmaceutic features. The MDTG nanoformulations are composed of hydrophobic prodrug particles dispersed in aqueous suspensions of polymeric excipients. The mechanism of drug release involves dissolution of the prodrug from the excipient follows efficient enzymatic cleavage generating the active agent. The benefits of the system include, without limitation, improved drug bioavailability and extended half-life.

Hydroxyl Group Deprotonation and Coupling to Fatty Acid

Dolutegravir (DTG) (2 g, 4.768 mmol, 1.0 equiv.) was dissolved in anhydrous dimethylformamide (20 mL) and cooled to 0° C. under argon. N,N diisopropylethylamine (1.66 mL, 9.536 mmol, 2.0 equiv.) was then added dropwise to the precooled solution of the drug. Myristoyl chloride (1.30 mL, 9.536 mmol, 2.0 equiv.) was then added to the deprotonated phenol solution. The mixture was gradually warmed to room temperature under stirring over 16 hours, concentrated, and purified by flash chromatography eluting with 80% EtOAc/Hex to give the prodrug in a chemical yield of 80%. The $^1$H-NMR spectrum of modified DTG prodrug (MDTG) showed the presence of a broad peak at 1.21-1.50 ppm and peaks corresponding to the aliphatic protons on the fatty acid moiety.

Formulation Development

The coating polymers used were poloxamer 407 (P407), 1,2-Distearoyl-sn-glycero-3-phosphocholine (DSPC), 1,2-distearoyl-sn-glycero-3-phosphoethanolamine-N-[carboxy (polyethylene glycol)-2000 (DSPE-PEG), and polyvinyl alcohol (PVA).

Based on proton NMR spectroscopy data, a drug to surfactant ratio of 100:6 by weight was used to manufacture nanoformulated MDTG and DTG. Briefly, 1-5% (w/v) MDTG or DTG and 0.06-0.3% (w/v) P407 were mixed in water. The premixed suspensions were formulated by wet milling or homogenizer at 20,000 psi pressure until desirable size and polydispersity index were achieved.

Nanoformulations were characterized for particle size, polydispersity index (PDI) and zeta potential by dynamic light scattering (FIG. 1). This was done using a Malvern Zetasizer, Nano Series Nano-ZS (Malvern Instruments Inc., Westborough, Mass.). Nanoparticle morphology was determined by scanning electron microscopy (SEM). Ultra performance liquid chromatography tandem mass-spectrometry (UPLC MS/MS) was used for drug quantitation. As seen in FIG. 1, the hydrophobicity of DTG was greatly improved upon derivatization into MDTG prodrug. Further, the improved hydrophobicity of MDTG facilitated production of stable formulations with high drug loading capacity.

Human monocytes were cultured in macrophage colony stimulating factor containing cell culture medium for 7-10 days in order to differentiate into macrophages (Balkundi et al. (2011) Intl. J. Nanomed., 6:3393-3404; Nowacek et al. (2009) Nanomed., 4(8):903-917). The macrophages were incubated with a range of formulations and native drugs. At each time point, adherent MDM were washed three times with 1 mL of PBS, scraped into 1 mL of fresh PBS and pelleted by centrifugation at 950×g for 8 minutes. The cell pellet was reconstituted in 200 µl of high performance liquid chromatography (HPLC)-grade methanol and probe sonicated followed by centrifugation at 20,000×g for 20 minutes. The supernatant was analyzed for drug content using HPLC (FIG. 2A and FIG. 2B). As seen in FIGS. 2A and 2B, conversion of DTG into the more hydrophobic MDTG and nanoparticle formation significantly improved intracellular accumulation of the drug to levels 100 fold higher than nanoformulated DTG.

MDM were treated with either 100 µM DTG, MDTG, P407-MDTG or FA-P407-MDTG for 8 hours. The cells were washed with PBS to remove excess of free drug and nanoparticles. The MDM were challenged with HIV-1ADA at a MOI of 0.01 infectious viral particles/cell for 18 hours on day 1, 5, 10 and 15. Progeny virion production was measured by reverse transcriptase (RT) activity in culture medium (Kalter et al. (1992) J. Clin. Microbiol., 30(4):993-995) (FIG. 2C). HIV-1 p24 protein antigen expression was assessed (Guo et al. (2014) J. Virol., 88(17):9504-9513). The MDM were washed with PBS and fixed with 4% paraformaldehyde for 15 minutes at room temperature. The cells were blocked using 10% BSA containing 1% Triton X-100 in PBS for 30 minutes at room temperature. Following blocking, cells were incubated with HIV-1 p24 mouse monoclonal antibodies (1:50; Dako, Carpinteria, Calif., USA) for overnight at 4° C., followed by 1 hour incubation at room temperature. HRP-labeled polymer anti-mouse secondary antibody (Dako EnVision® System) was added (one drop/well). Hematoxylin (500 µl per well) was added to counterstain the nuclei and images were captured using a Nikon TE300 microscope with a 20× objective (FIG. 2D). As seen in FIGS. 2C and 2D, significant improvements in MDM retention and antiretroviral efficacy were observed for nanoformulated MDTG.

Six weeks old balb/c mice were treated with 45 mg/kg of nanoformulated DTG or 67 mg/kg MDTG (equivalent to 45 mg/kg of DTG). Plasma was collected 1, 3, 7, 14, 21 and 28 days after administration. Tissues (liver, kidney, brain, spleen, lymph node, gut and muscle) were collected after sacrifice on day 28. Drug levels from plasma and tissues were assayed by UPLC-MS/MS (FIG. 3). Thus, a single intramuscular administration of nanoformulated MDTG into mice led to improved and sustained DTG blood concentrations of up to 10-fold higher than that of nanoformulated DTG. Notably, plasma DTG concentrations for nanoformulated MDTG at a month were still above the EC90 of DTG.

EXAMPLE 2

Herein, novel modified cabotegravir prodrugs (MCAB) are provided as well as their encapsulation into suitable excipients and stabilizers such as nanoformulated poloxamer 407 (P407-MCAB) or folic acid (FA) labeled nanoformulations (FA-P407-MCAB) for sustained and site specific drug delivery. The prodrugs comprise native drug conjugated to hydrophobic moieties via hydrolizable covalent bonds. The MCAB nanoformulations were easily taken up by human monocyte derived macrophages (MDM) with sustained drug release up to 10 days. In contrast, parent drug formulations were eliminated from MDM within a single day of treatment. Notably, MDM treated with nanoformulated MCAB exhibited enhanced antiretroviral activity compared to nanoformulated parent drug when MDM are infected at days 0, 2, 5 and 10 after drug treatment. HIV-1p24 was not detected in the NMCAB-treated group at any of these time points. The nanoformulated MCAB presented herein will improve combination antiretroviral therapy (cART) regimens that require multiple daily administrations by reducing pill burden, lowering the risk of viral rebound, limiting toxicities, and allowing for drug penetration into viral reservoirs.

Hydroxyl Group Deprotonation and Coupling to Fatty Acid

A solution of cabotegravir (CAB) (2 g, 4.93 mmol, 1.0 equiv.) in anhydrous dimethylformamide (20 mL) was cooled to 0° C. under argon. N,N diisopropylethylamine (1.7 mL, 9.86 mmol, 2.0 equiv.) was then added dropwise to the precooled solution of the drug. Myristoyl chloride (1.34 mL, 9.86 mmol, 2.0 equiv.) was then added to the deprotonated phenol solution. The mixture was gradually warmed to room temperature under stirring over 16 hours, concentrated, and purified by flash chromatography eluting with 80% EtOAc/Hex to give the prodrug in a chemical yield of 74%. The $^1$H-NMR spectrum of modified cabotegravir prodrug (MCAB) showing the presence of a broad peak at 1.20-1.50 ppm and peaks corresponding to the aliphatic protons on the fatty acid moiety.

Formulation Development

Coating polymers used were poloxamer 407 (P407), 1,2-Distearoyl-sn-glycero-3-phosphocholine (DSPC), 1,2-distearoyl-sn-glycero-3-phosphoethanolamine-N-[carboxy(polyethylene glycol)-2000 (DSPE-PEG), polyvinyl alcohol (PVA).

Based on proton NMR spectroscopy data, a drug to surfactant ratio of 100:6 by weight was used to manufacture nanoformulated MCAB and CAB. Briefly, 1-5% (w/v) MCAB or CAB and 0.06-0.3% (w/v) P407 were mixed in water. The premixed suspensions were formulated by wet milling or homogenizer at 20,000 psi pressure until desirable size and polydispersity index were achieved.

Nanoformulations were characterized for particle size, polydispersity index (PDI) and zeta potential by dynamic light scattering (DLS) (Table 1). This was done using a Malvern Zetasizer, Nano Series Nano-ZS (Malvern Instruments Inc, Westborough, Mass.). Nanoparticle morphology was determined by scanning electron microscopy (SEM). UPLC MS/MS was used for drug quantitation. As seen in Table 1, the hydrophobicity of CAB was greatly improved upon derivatization into MCAB. The improved hydrophobicity of MCAB facilitated production of stable formulations with high drug loading capacity.

TABLE 1

Nanoparticle characterization of P407-MCAB and FA-P407-MCAB by DLS.

| Formulations | Size (nm) | PDI | Charge (mV) |
|---|---|---|---|
| NMCAB | 314 | 0.360 | −23.3 |
| FA-NMCAB | 345 | 0.283 | −34.8 |

Human monocytes were cultured in macrophage colony stimulating factor containing cell culture medium for 7-10 days in order to differentiate into macrophages (Balkundi et al. (2011) Intl. J. Nanomed., 6:3393-3404; Nowacek et al. (2009) Nanomed., 4(8):903-917). The macrophages were incubated with a range of formulations and native drugs. At each time point, adherent monocyte-derived macrophage (MDM) were washed three times with 1 mL of PBS, scraped into 1 mL of fresh PBS and pelleted by centrifugation at 950×g for 8 minutes. The cell pellet was reconstituted in 200 µl of high performance liquid chromatography (HPLC)-grade methanol and probe sonicated followed by centrifugation at 20,000×g for 20 minutes. The supernatant was analyzed for drug content using HPLC (FIGS. 4A and 4B). The MCAB nanoformulations were easily taken up by human monocyte derived macrophages (MDM) with sustained drug release up to 10 days; whereas parent drug formulations were eliminated from MDM within a single day of treatment.

MDM were treated with either 100 µM CAB long acting parenteral (CAB-LAP), P407-CAB, P407-MCAB or FA-P407-MCAB for 8 hours. The cells were washed with PBS to remove excess of free drug and nanoparticles. The MDM were challenged with HIV-1ADA at a MOI of 0.01 infectious viral particles/cell for 18 hours on day 0, 2, 5 and 10. Progeny virion production was measured by reverse transcription (RT) activity in culture medium (Kalter et al.

(1992) J. Clin. Microbiol., 30(4):993-995). HIV-1 p24 protein antigen expression was assessed (Guo et al. (2014) J. Virol., 88(17):9504-9513) (FIG. 4C). The MDM were washed with PBS and fixed with 4% paraformaldehyde for 15 min at room temperature. The cells were blocked using 10% BSA containing 1% Triton X-100 in PBS for 30 min at room temperature. Following blocking, cells were incubated with HIV-1 p24 mouse monoclonal antibodies (1:50; Dako, Carpinteria, Calif., USA) for overnight at 4° C., followed by 1 hour incubation at room temperature. HRP-labeled polymer anti-mouse secondary antibody (Dako EnVision® System) was added (one drop/well). Hematoxylin (500 µl per well) was added to counterstain the nuclei and images were captured using a Nikon TE300 microscope with a 20× objective (FIG. 4D).

As seen in FIG. 4, conversion of CAB into more hydrophobic MCAB and nanoparticle formation significantly improved intracellular accumulation of the drug compared to CAB-LAP. Significant improvements in MDM retention and antiretroviral efficacy were also observed for nanoformulated MCAB. Notably, MDM treated with to nanoformulated MCAB exhibited enhanced antiretroviral activity compared to nanoformulated parent drug when MDM are infected at days 0, 2, 5 and 10 after drug treatment. HIV-1p24 was not detected in the NMCAB-treated group at any of these time points.

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A prodrug compound of the formula I-A

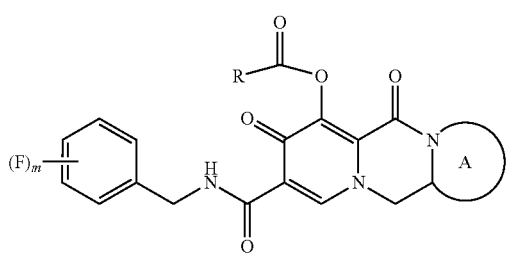

(I-A)

or pharmaceutically acceptable salt thereof
wherein ring A is selected from

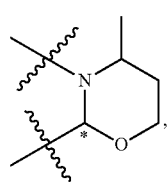

(II-A)

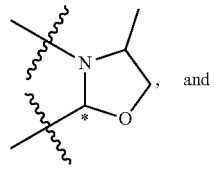

(II-B)

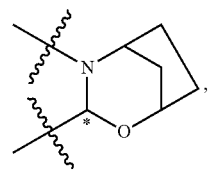

(II-C)

the stereochemistry of an asymmetric carbon represented by * shows R- or S-configuration, or a mixture thereof, m is 0, 1, 2, or 3, R is $(L)n-R^1$, L is selected from $C_3-C_{30}$ alkyl optionally substituted by 1-5 heteroatoms selected from N, S, and O, and $C_3-C_{30}$ alkyenyl optionally substituted by 1-5 heteroatoms selected from N, S, and O, n is 0 or 1, and $R^1$ is selected from H, aryl, cycloalkyl, and cycloalkenyl.

2. The prodrug compound or pharmaceutically acceptable salt of claim 1 wherein R is a saturated or unsaturated fatty acid residue.

3. The prodrug compound or pharmaceutically acceptable salt of claim 2 wherein the fatty acid residue is a residue selected from caprylic acid, capric acid, lauric acid, myristic acid, palmitic acid, stearic acid, arachidic acid, behenic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, and docosahexaenoic acid.

4. The prodrug compound or pharmaceutically acceptable salt of claim 3 wherein R is myristic acid.

5. The prodrug compound or pharmaceutically acceptable salt of claim 1 having the formula
(I-B):

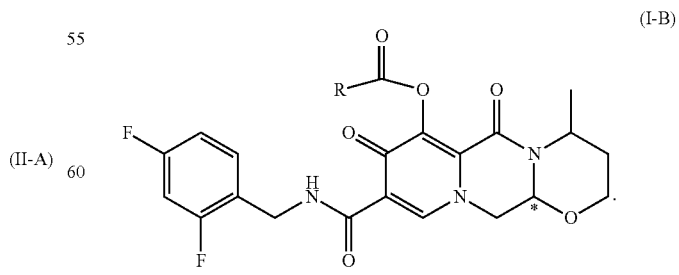

(I-B)

6. The prodrug compound or pharmaceutically acceptable salt of claim 1 having the formula (I-C):

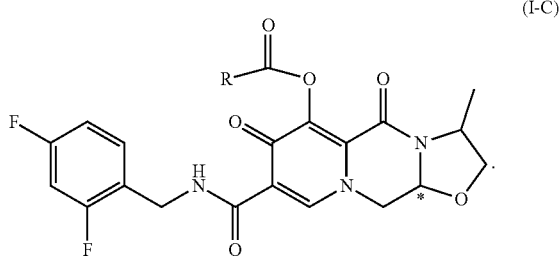

7. The prodrug compound or pharmaceutically acceptable salt of claim 1 having the formula (I-D):

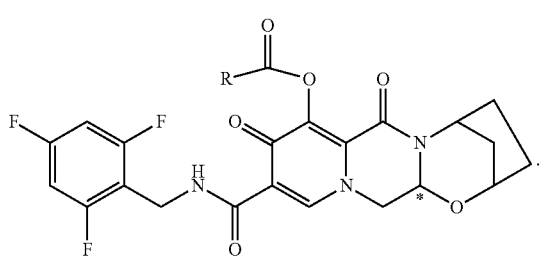

8. A nanoparticle comprising the prodrug compound or pharmaceutically acceptable salt of claim 1, and at least one surfactant.

9. The nanoparticle of claim 8, wherein the diameter of the nanoparticle is about 100 nm to 1 μm.

10. The nanoparticle of claim 8, wherein said surfactant is an amphiphilic block copolymer or PEGylated phospholipid.

11. The nanoparticle of claim 8, wherein said amphiphilic block copolymer comprises at least one block of poly(oxyethylene) and at least one block of poly(oxypropylene).

12. The nanoparticle of claim 8, wherein said surfactant is poloxamer 407.

13. The nanoparticle of claim 8, wherein said nanoparticle further comprises a surfactant linked to at least one targeting ligand.

14. The nanoparticle of claim 8, wherein said surfactant is linked to at least one targeting ligand.

15. The nanoparticle of claim 14, wherein said targeting ligand is a macrophage targeting ligand.

16. The nanoparticle of claim 15, wherein said macrophage targeting ligand is folate.

17. The nanoparticle of claim 8, wherein said nanoparticle comprises poloxamer 407 linked to folate.

18. The nanoparticle of claim 8, wherein said nanoparticle comprises at least about 80% prodrug compound by weight.

19. The nanoparticle of claim 18, wherein said nanoparticle comprises at least about 90% prodrug by weight.

20. The nanoparticle of claim 8 for use in treating an HIV infection.

21. A pharmaceutical composition comprising at least one nanoparticle of claim 8 and at least one pharmaceutically acceptable carrier.

22. The pharmaceutical composition of claim 21, wherein said pharmaceutical composition further comprises at least one other anti-HIV compound.

23. A method for treating an HIV infection in a subject in need thereof, said method comprising administering to said subject a prodrug compound or pharmaceutically acceptable salt of claim 1.

24. A method for inhibiting an HIV infection in a subject in need thereof, said method comprising administering to said subject a prodrug compound or pharmaceutically acceptable salt of claim 1.

25. A method for preventing an HIV infection in a subject in need thereof, said method comprising administering to said subject a prodrug compound or pharmaceutically acceptable salt of claim 1.

26. A method for treating an HIV infection in a subject in need thereof, said method comprising administering to said subject a nanoparticle of claim 8.

27. A method for inhibiting an HIV infection in a subject in need thereof, said method comprising administering to said subject a nanoparticle of claim 8.

28. A method for preventing an HIV infection in a subject in need thereof, said method comprising administering to said subject a nanoparticle of claim 8.

* * * * *

UNITED STATES PATENT AND TRADEMARK OFFICE
CERTIFICATE OF CORRECTION

PATENT NO. : 11,117,904 B2  
APPLICATION NO. : 16/304759  
DATED : September 14, 2021  
INVENTOR(S) : Edagwa et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 346 days.

Signed and Sealed this  
First Day of July, 2025

Coke Morgan Stewart  
*Acting Director of the United States Patent and Trademark Office*